(12) United States Patent
Bourquin et al.

(10) Patent No.: US 11,944,730 B2
(45) Date of Patent: Apr. 2, 2024

(54) BREAST STATUS DETERMINATION

(71) Applicant: KONINKLIJKE PHILIPS N.V., Eindhoven (NL)

(72) Inventors: Yannyk Parulian Julian Bourquin, Eindhoven (NL); Lucja Elżbieta Segaar, Oirschot (NL); Lili-Marjan Brockhuis, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 922 days.

(21) Appl. No.: 15/733,395

(22) PCT Filed: Jan. 11, 2019

(86) PCT No.: PCT/EP2019/050601
§ 371 (c)(1),
(2) Date: Jul. 20, 2020

(87) PCT Pub. No.: WO2019/145163
PCT Pub. Date: Aug. 1, 2019

(65) Prior Publication Data
US 2021/0093759 A1 Apr. 1, 2021

(30) Foreign Application Priority Data
Jan. 24, 2018 (EP) ..................................... 18153139

(51) Int. Cl.
*A61M 1/06* (2006.01)
(52) U.S. Cl.
CPC .............. *A61M 1/06* (2013.01); *A61M 1/066* (2014.02); *A61M 1/06935* (2021.05);
(Continued)

(58) Field of Classification Search
CPC .... A61M 1/06; A61M 1/066; A61M 1/06935; A61M 1/0697; A61M 2205/18;
(Continued)

(56) References Cited

U.S. PATENT DOCUMENTS

| 2005/0059928 A1 | 3/2005 | Larsson |
| 2017/0172485 A1 | 6/2017 | Makower et al. |

(Continued)

FOREIGN PATENT DOCUMENTS

| EP | 2606816 | 6/2013 |
| JP | 2011221801 | 11/2011 |

(Continued)

OTHER PUBLICATIONS

International Search Report and Written Opinion dated Feb. 20, 2019 For International Application No. PCT/EP2019/050601 Filed Jan. 11, 2019.

*Primary Examiner* — Shefali D Patel
*Assistant Examiner* — Rachel T. Smith

(57) ABSTRACT

The present invention relates to a breast status determination device (10'). The breast status determination device (10') comprises a breast shield (16'), a nipple elongation measurement unit (17'), and a breast status determination unit (20'). The breast shield (16') can receive a breast (12) of a user (14) therein. The nipple elongation measurement unit (17') can measure an elongation of a nipple of the breast (12) received in the breast shield (16') for a specific pressure in the breast shield (16') during a milk extraction session. The breast status determination unit (20') can determine a status of the breast (12) based on the elongation of the nipple (26). The breast status determination device (10') can allow estimating of milk left in the breast during the milk extraction session, when the breast (12) is empty, and whether a milk ejection reflex is present or absent in the breast (12).

14 Claims, 7 Drawing Sheets

(52) U.S. Cl.
CPC ....... *A61M 1/0697* (2021.05); *A61M 2205/18* (2013.01); *A61M 2205/3306* (2013.01); *A61M 2205/3331* (2013.01); *A61M 2205/70* (2013.01); *A61M 2230/00* (2013.01)

(58) Field of Classification Search
CPC .. A61M 2205/3306; A61M 2205/3331; A61M 2205/70; A61M 2230/00; A61M 2205/3375; A61M 2205/583; A61M 1/062; A61M 1/064; A61M 1/067; A61M 1/068; A61M 1/069; A61M 1/0693; A61M 2205/50; A61M 2210/1007; A61J 13/00
See application file for complete search history.

(56) References Cited

U.S. PATENT DOCUMENTS

2017/0368244 A1* 12/2017 Elad ................. A61M 1/066
2020/0078503 A1*  3/2020 Bartlett ............. A61M 1/062

FOREIGN PATENT DOCUMENTS

| WO | 2009027868 | 3/2009 |
|----|------------|--------|
| WO | 2016/044368 | 3/2016 |
| WO | 2016/145173 | 9/2016 |
| WO | 2017/139437 | 8/2017 |

* cited by examiner

BREAST STATUS DETERMINATION

CROSS REFERENCE TO RELATED APPLICATIONS

This application is the U S. National Phase application under 35 U.S.C. § 371 of International Application No. PCT/EP2019/050601 filed Jan. 11, 2019, published as WO 2019/145163 on Aug. 1, 2019, which claims the benefit of European Patent Application Number 18153139.3 filed Jan. 24, 2018 These applications are hereby incorporated by reference herein.

FIELD OF THE INVENTION

The present invention relates to a breast status determination device, a breast pump with a breast status determination device, a method for operating a breast pump with a breast status determination device, and a computer program.

BACKGROUND OF THE INVENTION

Breast pumps can be used to extract milk from a breast of a mother. To start milk ejection from the breast, a milk ejection reflex (MER) also called let-down reflex has to be triggered. For example the suckling pattern of a baby, i.e. applying positive and negative pressure to a nipple of the breast, can stimulate the MER. In the MER, oxytocin (OT) is produced which stimulates contraction of myoepithelial cells surrounding alveoli in the breast which hold milk. Due to the MER, milk is transported from the alveoli through ducts and sacs to the nipple. A breast pump can stimulate the MER by mimicking the suckling pattern of the baby in a mechanical way, i.e., performing cycles of suction and release by applying increased pressure and reduced pressure. Suction applied to the nipple or pressure applied to the breast allows to extract the milk. The milk flow during a milk extraction session is irregular as milk is only transported from the alveoli to the nipple during the MER. A breast that is not fully emptied after breastfeeding or milk extraction increases the risk of breast inflammation called mastitis.

US 2017/0172485 A1 and WO 2016/044368 A1 show a system and method for assessing milk volume changes within a breast. A device is attached to the breast. The device includes an expansible portion and a sensor for sensing an amount of expansion or contraction of skin of the breast to which the device is attached. An amount of expansion or contraction of the skin to which the device is attached is sensed and a volume change of the breast is calculated based on the amount of contraction or expansion sensed. An amount of milk expressed from the breast can be calculated based on the volume change of the breast.

SUMMARY OF THE INVENTION

It can be seen as an object of the present invention to provide a breast status determination device, a breast pump with a breast status determination device, a method for operating a breast pump with a breast status determination device, and a computer program, which allow determining a status of a breast during a milk extraction session.

In a first aspect of the present invention a breast status determination device is presented. The breast status determination device comprises a breast shield, a nipple elongation measurement unit, and a breast status determination unit. The breast shield is configured for receiving a breast of a user therein. The nipple elongation measurement unit is configured for measuring an elongation of a nipple of the breast received in the breast shield for a specific pressure in the breast shield during a milk extraction session. The breast status determination unit is configured for determining an estimated breast emptiness of the breast of the user, a presence or absence of a milk ejection reflex, or the estimated breast emptiness of the breast of the user and the presence or absence of the milk ejection reflex of the breast of the user as a status of the breast of the user based on the elongation of the nipple of the breast of the user.

The specific pressure in the breast shield can be provided as a predetermined pressure applied to the breast shield or the specific pressure in the breast shield can be measured in the breast shield, e.g. using a pressure estimation unit.

The breast status determination device can be configured to be used by mammals such as humans or non-human mammals, such as cattle, goats, sheep, or any other non-human mammal.

Since the breast status determination unit is configured for determining the status of the breast of the user based on the elongation of the nipple of the breast of the user and the nipple elongation measurement unit is configured for measuring the elongation of the nipple for the specific pressure in the breast shield during the milk extraction session, the status of the breast can be determined during the milk extraction session. Tis allow s to react on the determined status of the breast during the milk extraction session. e.g., changing parameters of the milk extraction and/or ending the milk extraction session in dependence of the determined status of the breast of the user.

The determined status of the breast of the user can be the estimated breast emptiness of the breast of the user, the detected presence or absence of a MER, or the estimated breast emptiness of the breast of the user and the detected presence or absence of the MER of the breast of the user. The breast status determination unit can be configured for estimating the breast emptiness of the breast of the user, for detecting the presence or absence of the MER, or for estimating the breast emptiness of the breast of the user and for detecting the presence or absence of the MER based on the elongation of the nipple of the breast of the user. The breast status determination unit can comprise a breast emptiness estimation unit configured for estimating the breast emptiness of the breast of the user based on the elongation of the nipple of the breast of the user and/or a MER detection unit configured for detecting the presence or absence of the MER based on the elongation of the nipple of the breast of the user.

Breast emptiness corresponds to an amount of milk left in the breast of the user. The amount of milk left in the breast can for example be denoted as a volume in $cm^3$, an amount of fluid in liter, or a ratio between an amount of milk left in the breast and a total amount of milk in the breast at the beginning of the milk extraction session. During the milk extraction session, milk is extracted from the breast and the amount of milk left in the breast is lowered until the milk extraction session ends and/or all milk is extracted.

Milk can be extracted from the breast during the milk extraction session for example by applying cycles of alternating increased pressure and reduced pressure to the breast received in the breast shield, i.e., applying suction and release to the nipple, e.g., using a pressure source such as a vacuum pump. Increased pressure is a pressure that is higher than reduced pressure and reduced pressure is a pressure lower than the pressure of the surroundings of the breast shield, e.g., pressure below 1 bar. The increased pressure can be lower than the pressure of the surroundings of the breast shield in order to provide a baseline suction, i.e., providing a suction force that is lower than suction force during reduced pressure. Alternatively the increased pressure can be a pressure that is higher than the pressure of the surroundings of the breast shield. The nipple elongates due to suction applied to the nipple. The elongation of the nipple is to be understood as the change of a position of a tip of the nipple in the direction of the suction applied to the nipple. The elongation of the nipple depends on applied suction force caused by the specific pressure in the breast shield and the breast emptiness of the breast of the user. This allows to detect when the breast is empty by providing the specific pressure in the breast shield and measuring when the elongation of the nipple reaches a predetermined threshold value that corresponds to an empty breast for the specific pressure in the breast shield. The predetermined threshold value for the elongation of the nipple that corresponds to an empty breast for a specific pressure in the breast shield can for example be determined in previous milk extraction sessions.

In order for milk to be extractable from the breast a MER needs to be triggered. It is possible that MER is not present in some cycles of suction and release. If MER is not present, no milk will be transported from the alveoli to the nipple and only milk that has already been transported to the nipple, e.g. milk in ducts and sacs of the breast, can be extracted from the breast. If MER is not present for some time, no milk can be extracted from the breast, i.e. there is no milk left in the ducts and sacs, no milk flow, and the breast emptiness is unchanged. If no milk is extracted from the breast, the elongation of the nipple does not change for equal suction applied to the nipple, i.e. the specific pressure in the breast shield, in subsequent cycles of alternating increased pressure and reduced pressure. This allows to detect whether MER is present or not by using the nipple elongation measurement unit for determining whether elongation of the nipple changes for equal suction applied to the nipple in subsequent cycles of alternating increased pressure and reduced pressure under the condition that the breast is not empty. The breast can for example be determined to be not empty when the elongation of the nipple is below the predetermined threshold value for the elongation of the nipple that corresponds to the empty breast for the specific pressure in the breast shield or when a duration of the current milk extraction session is of a length that ensures that the breast is not empty, e.g., when the duration of the current milk extraction session is below a predetermined duration threshold value, for example below 3 minutes, such as below 2 minutes or below 1 minute. The predetermined duration threshold value can for example be determined from previous milk extraction sessions by measuring the respective duration until the breast is empty.

The elongation of the nipple can be measured for several cycles of alternating increased and reduced pressure in order to study the elongation of the nipple over time. The elongation of the nipple during a cycle of increased and reduced pressure is maximal when a maximal reduced pressure is provided in the breast shield and suction force on the nipple becomes maximal. The maximal reduced pressure is to be understood as the maximal reduced pressure that is provided in the breast shield in the respective cycle of alternating increased and reduced pressure, e.g., generated by a pressure source such as a vacuum pump. The same maximal reduced pressure can be provided in the breast shield in all or at least some of the cycles of alternating increased and reduced pressure which allows to use the maximal reduced pressure as specific pressure in the breast shield for comparing the elongations of the nipple of different cycles, i.e., the elongation of the nipple can be compared for maximal suction applied to the nipple for all cycles or at least some of the cycles. Using a very low reduced pressure, e.g., a pressure value significantly below 1 bar, improves accuracy of the elongation measurement as the elongation of the nipple is increased. Using a high reduced pressure. e.g., a pressure value only slightly below 1 bar, for comparing the elongation of the nipple allows to lower the wear on the nipple of the user and can be more comfortable for the user.

If the breast is empty, i.e., no extractable milk is left in the breast, the elongation of the nipple for the specific pressure in the breast shield reaches a maximum for the milk extraction session. A breast emptiness corresponding to an empty breast, e.g., breast emptiness 100%, can be detected when elongation of the nipple reaches the predetermined threshold value corresponding to the empty breast for the specific pressure in the breast shield or when the elongation of the nipple for the specific pressure in the breast shield is maximal and not changing between subsequent cycles of increased pressure and reduced pressure anymore for a predetermined number of cycles or a predetermined time. The number of cycles or predetermined time has to be large enough in order to ensure that no milk is left in the breast which may be not extracted in that period of time due to a missing MER. Alternatively the breast emptiness corresponding to the empty breast can be detected when the elongation of the nipple for the specific pressure in the breast shield is maximal and not changing between two subsequent cycles of increased pressure and reduced pressure anymore in which presence of the MER is detected.

The amount of milk at the beginning of the milk extraction session, corresponding to a full breast, can for example be estimated based on previous milk extraction sessions, e.g. by measuring the amount of extracted milk in previous milk extraction sessions. The breast emptiness can for example be estimated based on comparing the currently measured elongation of the nipple for the specific pressure in the breast shield and the maximal elongation of the nipple for the specific pressure in the breast shield that is expected at the end of the milk extraction session, i.e., the maximal elongation of the nipple for the specific pressure in the breast shield for the empty breast. The maximal elongation of the nipple for the specific pressure in the breast shield expected at the end of the milk extraction session can be based on measured elongations of the nipple for the specific pressure in the breast shield at the end of previous milk extraction sessions. The elongation of the nipple for the specific pressure in the breast shield, measured in previous milk extraction sessions can furthermore be correlated to ratio of milk extracted from the breast during the milk extraction session, e.g., by measuring the amount of extracted milk. Alternatively breast emptiness can be estimated based on a breast emptiness estimation function that uses elongation of the nipple and the specific pressure in the breast shield as input parameters and provides breast emptiness as output parameter. Coefficients of the breast emptiness estimation function can for example be determined based on training data collected during previous milk extraction sessions and using, e.g., machine learning, regression analysis, or any other method for deriving coefficients based on training data. Since the breast status determination unit can be configured for estimating breast emptiness of the breast of the user based on the elongation of the nipple of the breast of the user and the nipple elongation measurement unit is configured for measuring the elongation of the nipple for the specific pressure in the breast shield during the milk extraction session, breast emptiness can be estimated during the milk extraction session. This allows to end the milk extraction session when a predetermined breast emptiness is reached and allows to reduce the risk of mastitis caused by prematurely ending the milk extraction session when the breast is not empty.

The breast status determination unit can be configured for adapting a breast shield setting in dependence of the determined status of the breast of the user. The breast shield setting can comprise values for a pressure in the breast shield, a pressure applied to the breast shield, and/or for other parameters of the milk extraction session such as a frequency and/or an intensity of a peristaltic action and/or massaging action of a collapsible membrane at the breast shield. This allows to adapt the parameters of the milk extraction session in order to improve the extraction of milk, for example by adapting the breast shield setting for stimulating the MER, when absence of MER is detected, by adapting the breast shield settings for extracting milk from the breast, when presence of MER is detected, or by adapting the breast shield settings for stopping extraction of milk when the estimated breast emptiness indicates that the breast is empty. A breast shield setting for stimulating the MER can for example be to apply a high reduced pressure with a high frequency of alternating cycles of increased pressure and reduced pressure such that a low suction force is applied to the nipple and/or massaging action of a collapsible membrane acting on the breast. A breast shield setting for extracting milk from the breast can for example be to apply a very low reduced pressure with a low frequency of alternating cycles of increased pressure and reduced pressure such that a high suction force is applied to the nipple and/or peristaltic action of a collapsible membrane acting on the breast. The breast shield setting can for example be transmitted to an external device, such as a pressure source of a breast pump connected with the breast status determination device in order to control the pressure applied to the breast shield by the pressure source. The breast shield setting can for example be used to control a pressure generation setting of a pressure source, such as a pressure source of a breast pump.

The breast status determination device can comprise a control unit. The control unit can be part of the nipple elongation measurement unit or the breast status determination unit. The control unit can be configured to control the units of the breast status determination device. The control unit can comprise a processor for processing data. The control unit can comprise a user interface for allowing user interaction. Alternatively, the control unit can be connected to a user interface. The user interface can be configured to receive user input, e.g. selection or adjustment of predetermined threshold values of elongation of the nipple or predetermined threshold values of breast emptiness of the breast of the user and to generate control signals based on the user input. The control unit can be configured to transmit the control signals to the units of the breast status determination device in order to control the units of the breast status determination device.

The control unit can be configured to activate the nipple elongation measurement unit when the breast of the user is received in the breast shield. Alternatively. or additionally the control unit can be configured to activate the nipple elongation measurement unit when a control signal provided by the user interface is received. The control unit can be configured to deactivate the breast status determination device when the breast of the user is removed from the breast shield. Alternatively or additionally the control unit can be configured to deactivate the breast status determination device when a control signal for deactivating the breast status determination device is received, e.g., provided by the user interface. The control unit allows control of the breast status determination device.

The breast status determination device can comprise a breast status indication unit configured for indicating to the user the determined status of the breast of the user. The breast status indication unit can comprise a visual indication unit, an audio indication unit, an automatic switch-off unit, any other breast status indication unit, such as a haptic indication unit, or any combination of visual indication unit, audio indication unit, automatic switch-off unit, or any other breast status indication unit.

The visual indication unit can for example be a gauge, a lighting unit, or a display configured for showing a gauge that represents the determined status. e.g. breast emptiness, of the breast of the user. The visual indication unit can be configured for visually indicating the determined status. e.g. breast emptiness, detected presence of the MER, or detected absence of the MER, of the breast of the user.

The audio indication unit can for example be an alarm configured for generating a sound for a specific determined status of the breast of the user, e.g., when breast emptiness reaches a predetermined threshold value, for example when the breast is empty or when for example an amount of 30% or 30 ml of milk is left in the breast. This allows to indicate a current determined status, e.g. estimated breast emptiness, to the user, so that the user can decide when to end the milk extraction session, for example if the user wants to have milk left for subsequent breast feeding shortly after the milk extraction session. The breast status indication unit can for example be provided with control signals for setting the predetermined threshold value of breast emptiness in order to allow to control when indication of breast emptiness is provided by the breast status indication unit. The automatic switch-off unit can be configured to automatically end the milk extraction session when a predetermined status of the breast of the user is determined, e.g., when the breast of the user is empty, or when the breast emptiness reaches the predetermined threshold value. The automatic switch-off unit can be configured to generate a control signal for switching off a pressure source, such as a vacuum pump, connected to the breast shield in order to automatically end the milk extraction session when the predetermined status of the breast of the user is determined, e.g., when the breast of the user is empty or when the breast emptiness reaches the predetermined threshold value. The breast status indication unit can be connected to the control unit. The control unit can be configured to perform the functions of the automatic switch-off unit.

The breast status indication unit can be configured for indicating to the user when the breast of the user is empty. This allows indicating to the user when the user can end the milk extraction session.

The nipple elongation measurement unit can be configured to be arranged at the breast of the user, e.g. via an attachment unit such as a suction pad or via incorporating the nipple elongation measurement unit or parts of the nipple elongation measurement unit in the breast shield. The nipple elongation measurement unit can alternatively be arranged in proximity to the breast of the user in order to measure the elongation of the nipple of the breast of the user. The nipple elongation measurement unit can be arranged in or on the breast shield, such as inside of the breast shield material or on an inner side of the breast shield which is in contact with the skin of the breast of the user when the breast shield received the breast of the user or on an outer side of the breast shield opposite of the inner side.

The nipple elongation measurement unit can be configured for measuring the elongation of the nipple of the breast received in the breast shield for the specific pressure in the breast shield during the milk extraction session based on an indirect measurement. An indirect measurement is a measurement without physical contact between the nipple and the nipple elongation measurement unit. This allows to avoid friction between solid surfaces of the breast shield and the nipple elongation measurement unit which can occur when the nipple elongation measurement unit is in physical contact with the nipple. Furthermore this allows a more comfortable use of the breast status determination device and an improved user experience. Indirect measurements can for example be performed by using a camera, a distance sensor, or a pressure estimation unit for measuring the elongation of the nipple.

The nipple elongation measurement unit can comprise a camera, a distance sensor, a pressure estimation unit, a nipple shape measurement unit, or any combination of them.

The camera is configured for recording images of the nipple of the breast of the user during the milk extraction session. Alternatively, the nipple elongation measurement unit can be connected to an external camera, such as a camera of a mobile phone, which is configured for recording images of the nipple of the breast of the user during the milk extraction session and to provide the recorded images to the nipple elongation measurement unit if the nipple elongation measurement unit comprises or is connected to a camera and the camera is arranged such that the breast shield is in the field of view between the camera and the nipple of the breast, the breast shield is translucent to light carrying image information from the nipple of the breast to the camera. The camera allows to estimate the elongation of the nipple for the specific pressure in the breast shield based on recorded images during the milk extraction session.

The distance sensor can be arranged opposite of a tip of the nipple of the breast of the user and axially aligned to the direction in which the nipple elongates during the milk extraction session. The distance sensor can be an optical distance sensor, an acoustic distance sensor, or any other type of distance sensor. The distance sensor can for example be a proximity sensor such as a radar, a sonar, or an ultrasound sensor. The distance sensor can be configured to measure a distance between the distance sensor and the tip of the nipple of the breast of the user during the milk extraction session. The distance sensor can for example be configured to measure the distance between the distance sensor and the tip of the nipple of the breast of the user during the milk extraction session, based on changes of an electromagnetic field or a time of flight measurement of a signal. The distance sensor can be configured for measuring a time of flight of a signal, such as ultrasound or an infrared signal between the distance sensor and the tip of the nipple of the breast of the user during the milk extraction session. The distance sensor allows estimating the elongation of the nipple for the specific pressure in the breast shield based on the distance between the distance sensor and the tip of the nipple of the breast of the user during the milk extraction session. The distance between the distance sensor and the tip of the nipple of the breast of the user during the milk extraction session can for example be measured based on changes of the electromagnetic field or based on time of flight measurements during the milk extraction session.

The pressure estimation unit can comprise one or more pressure sensors. The pressure estimation unit can be configured to measure the specific pressure in the breast shield. This allows to measure the specific pressure in the breast shield for example if the pressure applied to the breast shield, e.g. by a pressure source such as a vacuum pump, is not known. The pressure estimation unit can furthermore be configured to measure the pressure outside of the breast shield. This allows to measure a pressure applied to the breast shield and/or a pressure of the surroundings of the breast shield. The elongation of the nipple can for example be measured using the camera, the distance sensor, the nipple shape measurement unit, or any combination of them for a pressure applied to the breast shield that is not known and the pressure in the breast shield can be measured by the pressure estimation unit. This allows measuring the elongation of the nipple in dependence of the specific pressure in the breast shield for a pressure applied to the breast shield that is not known.

Alternatively or additionally the pressure estimation unit can be configured for estimating a drop of pressure within the breast shield in which the breast of the user is received during the milk extraction session. The drop of pressure depends on a volume formed between the breast and the breast shield. The volume can for example be provided by a nipple tunnel. The volume between the breast and the breast shield decreases as the nipple elongates. The pressure estimation unit allows to estimate the elongation of the nipple for the specific pressure in the breast shield based on a change of the volume between the breast and the breast shield.

Alternatively or additionally the pressure estimation unit can be configured to detect whether the breast is correctly received in the breast shield. The pressure estimation unit can be configured to compare a pressure measured in the breast shield with a pressure applied to the breast shield. e.g., by a pressure source such as a vacuum pump. Based on the difference of measured and applied pressure the pressure estimation unit can determine whether the breast is correctly received in the breast shield. i.e., whether the breast shield is correctly positioned on the breast. This allows to indicate to the user whether the breast shield should be rearranged on the breast in order to ensure correct operation of the breast status determination device.

If the nipple elongation measurement unit measures the elongation of the nipple using the camera, the distance sensor, the nipple shape measurement unit, or any combination of them for a predetermined pressure applied to the breast shield, the pressure in the breast shield can be influenced by the elongation of the nipple and presence of milk in the breast shield, e.g. due to a changed volume in the breast shield. i.e. a changed volume between the breast and the breast shield. The pressure measured by the pressure estimation unit can be used to correct for the changed volume in the breast shield. Alternatively the effect of the changed volume on a pumping action of a pressure source, e.g. a vacuum pump, can be used to correct for the changed volume in the breast shield. As the volume in the breast shield decreases with increasing elongation, the volume that is required to be extracted by the pressure source such as a vacuum pump from the breast shield is lower in order to reach the predetermined pressure. This can for example be detected by measuring the duration to reach a maximal reduced pressure applied to the breast shield.

The nipple shape measurement unit can be configured for measuring a shape of the nipple of the breast of the user during the milk extraction session. The elongation of the nipple depends on the shape of the nipple. i.e. when the nipple elongates, also the shape of the nipple is changed. The nipple shape measurement unit allows to estimate the elongation of the nipple for the specific pressure in the breast shield based on a change of the shape of the nipple for the specific pressure in the breast shield during the milk extraction session. The nipple shape measurement unit can comprise a collapsible membrane and a membrane shape measurement unit. The collapsible membrane comprises or forms at least one opening in order to allow milk extracted from the breast to pass. The collapsible membrane and the membrane shape measurement unit can be configured for measuring the elongation of the nipple for the specific pressure in the breast shield during the milk extraction session. The collapsible membrane can be arranged at the breast shield and can be configured to conform to a shape of the breast when the breast is received in the breast shield. Furthermore the collapsible membrane can be configured to provide that a shape of the collapsible membrane conforms to a shape of the breast of the user during the milk extraction session. The collapsible membrane can comprise a reversibly deformable material.

The collapsible membrane can be configured to extend from an unextended state to an extended state when the breast is received in the breast shield. The collapsible membrane can be configured to cover in the unextended state an area that is smaller than the surface area of the empty breast and to conform to the shape of the breast in the extended state. The collapsible membrane can be configured to conform to the shape of the breast during the milk extraction session by reducing the area covered by the collapsible membrane, when milk is extracted from the breast and the breast reduces in size and surface area. The membrane shape measurement unit can be configured for measuring the shape of the collapsible membrane during the milk extraction session in order to measure the elongation of the nipple for the specific pressure in the breast shield.

Alternatively the collapsible membrane can also be configured for pressing on the nipple and/or the breast to a certain extend in order to perform a peristaltic action or massaging action on the nipple and/or breast for stimulating the MER and/or for supporting the extraction of milk from the nipple. The peristaltic action supports the extraction of milk from the nipple and the massaging action stimulates the MER. Such a collapsible membrane is for example disclosed in WO 20110/109398 A1 which is incorporated herein by reference. The membrane shape measurement unit can be configured to correct the additional deformation caused by the pressure on the nipple and/or breast in order to measure the elongation of the nipple for a specific pressure in the breast shield. Alternatively the membrane shape measurement unit can also be configured to use the pressing on the nipple and/or breast for obtaining information on the stiffness of the nipple and/or breast. This can be used to improve the measurement of the elongation of the nipple.

Alternatively the breast status determination device can be configured to ensure that the collapsible membrane conforms to the shape of the breast during the whole milk extraction session by providing that an increased pressure in form of a baseline suction is provided in the breast shield in alternating cycles of increased pressure and reduced pressure. The collapsible membrane can then be in continuous contact with the breast and the nipple. The membrane shape measurement unit can be configured to measure the shape of the nipple when the collapsible membrane is not used for peristaltic action or massaging action, e.g., during increased pressure in form of baseline suction.

The membrane shape measurement unit can comprise strain sensors arranged on the collapsible membrane for measuring strain. The membrane shape measurement unit can be configured to measure the shape of the collapsible membrane based on strain measurements at the strain sensors. The strain measurements allow for example to derive a local curvature of the collapsible membrane which can be used to measure the shape of the collapsible membrane. The membrane shape measurement unit can be configured for measuring the local curvature of the part of the collapsible membrane in physical contact with the nipple in order to measure the elongation of the nipple for the specific pressure in the breast shield. Alternatively or additionally the membrane shape measurement unit can comprise an accelerometer for estimating the shape of the collapsible membrane. The shape of the breast and the shape of the nipple depend on breast emptiness. Since the shape of the collapsible membrane conforms to the shape of the breast, also the shape of the collapsible membrane depends on breast emptiness. The nipple shape measurement unit allows to measure the elongation of the nipple for the specific pressure in the breast shield based on a measured change of the shape of the nipple.

The membrane shape measurement unit can also be configured for measuring the shape of the breast during the milk extraction session in order to improve estimation of breast emptiness. The membrane shape measurement unit can be configured to use the estimated shape of the collapsible membrane in order to measure the shape of the breast. The shape of the breast depends on breast emptiness. This allows to improve estimation of breast emptiness, as additional information can be provided for estimating breast emptiness of the breast of the user. The shape of the breast can for example be an additional input parameter to the breast emptiness estimation function or the shape of the breast together with the elongation of the nipple and the specific pressure in the breast shield can be correlated to breast emptiness.

The nipple shape measurement unit can allow to measure the shape of the breast and the shape of the nipple. The measured shape of the breast can be used to improve estimation of breast emptiness and the measured shape of the nipple can be used to measure the elongation of the nipple for the specific pressure in the breast shield. The collapsible membrane and the membrane shape measurement unit can be used to measure both the shape of the breast and the shape of the nipple or only one of the shape of the breast and the shape of the nipple. If the nipple shape measurement unit is configured to only measure the shape of the breast, the nipple elongation measurement unit has to comprise an additional unit for measuring the elongation of the nipple during the milk extraction session, e.g., a camera, a distance sensor, a pressure estimation unit, or a nipple shape measurement unit configured for measuring the shape of the nipple, in order to measure the elongation of the nipple for the specific pressure in the breast shield during the milk extraction session.

The breast status determination unit can be configured to be arranged at the breast of the user, e.g. via an attachment unit such as a suction pad or via incorporating the breast status determination unit or parts of the breast status determination unit in the breast shield. Alternatively the breast status determination unit can also be arranged on a server, computer, mobile phone, or other external network device. The breast status determination unit is configured to receive the measured elongation of the nipple of the breast of the user for the specific pressure in the breast shield from the nipple elongation measurement unit. The breast status determination unit can be connected to the nipple elongation measurement unit. The connection can be wire based or wireless. This allows providing the measured elongation of the nipple of the breast of the user for the specific pressure in the breast shield from the nipple elongation measurement unit to the breast status determination unit in order to determine the status of the breast of the user.

The breast status determination unit can comprise a memory. The memory can be a part of the control unit. Alternatively, the breast status determination unit can be connected to a memory. The memory can store at least one value of breast emptiness in dependence of the elongation of the nipple and the specific pressure in the breast shield. Alternatively or additionally the memory can store a breast emptiness estimation function with the elongation of the nipple and the specific pressure in the breast shield as input and breast emptiness as output. The at least one value of breast emptiness in dependence of the elongation of the nipple and the specific pressure in the breast shield can be recorded in previous milk extraction sessions in order to use the at least one value of breast emptiness in subsequent milk extraction sessions and/or as training data. Coefficients for the breast emptiness estimation function can for example be determined based on training data collected during previous milk extraction sessions and using, e.g., machine learning, regression analysis, or any other method for deriving coefficients based on training data.

The breast shield has a shape that allows to receive the breast of the user. The breast shield can for example be funnel shaped. The breast shield can be made from a resilient material such as polyurethane or silicone. This allows a better fit to the breast of the user and is more comfortable. The breast shield can comprise a nipple tunnel. The nipple tunnel can be configured to receive the nipple of the breast of the user. The nipple tunnel allows a more accurate measurement of the elongation of the nipple and improved milk extraction.

The breast status determination device can comprise a power source. The power source can be configured for powering the nipple elongation measurement unit, the breast status determination unit, the control unit, the breast status indication unit, or any combination of them. The power source can for example be a battery. This allows mobile use of the breast status determination device.

In a further aspect of the present invention, a breast pump is presented. The breast pump comprises a breast status determination device according to a representative embodiment of the breast status determination device and a pressure source. The pressure source is in air-ducting connection to the breast shield and configured for generating cycles of alternating increased pressure and reduced pressure in the breast shield to extract milk from the breast of the user.

The pressure source can be a manually operated pump or an automatic pressure source, such as an electric vacuum pump. This allows to extract milk from the breast of the user.

The pressure source can be configured to perform a suckling pattern in order to stimulate MER of the breast of the user and/or to extract milk from the breast. The suckling pattern preferably is cyclic. The pressure source can be configured to generate cycles of alternating increased pressure and reduced pressure in the breast shield such that suction and release forces on the nipple of the breast of the user alternate in the breast shield.

The breast pump can comprise a breast pump control unit. The breast pump control unit can be configured to control the breast pump. The breast pump control unit can be configured to control the pressure source, the breast status determination device, or the pressure source and the breast status determination device. Alternatively the control unit of the breast status determination device can be configured to control the pressure source. The breast pump control unit can comprise a user interface for user interaction. This allows central control of all components of the breast pump via the breast pump control unit.

The breast pump control unit can be configured to synchronize a moment of sampling of the elongation of the nipple with the specific pressure in the breast shield generated by the pressure source. The specific pressure can for example be the maximal reduced pressure provided in the breast shield in the respective cycle of alternating increased pressure and reduced pressure. Alternatively or additionally, the nipple elongation measurement unit can be configured to synchronize a moment of sampling of the elongation of the nipple with the specific pressure in the breast shield generated by the pressure source.

The elongation of the nipple for the specific pressure in the breast shield can be measured and the measured elongations between various cycles of alternating increased pressure and reduced pressure can be compared as the elongation of the nipple is cyclic following the cycles of alternating increased pressure and reduced pressure in the breast shield. In the moment in which a maximal pressure in the breast shield is generated by the pressure source, the elongation of the nipple has a local maximum. This allows to measure maxima of the elongation of the nipple and to compare the maxima. Measuring maxima of the elongation of the nipple, i.e., using the same maximal reduced pressure as specific pressure in the cycles of alternating increased pressure and reduced pressure that are to be compared, allows an improved accuracy. Furthermore in each subsequent cycle during the milk extraction session in which milk flow is present, the maximal elongation of the nipple is increased as milk is extracted from the breast and elongation of the nipple depends on the breast emptiness and the pressure in the breast shield. A global maximum of the elongation of the nipple for the specific pressure in the breast shield is reached when the breast is empty. This allows to estimate when the breast is empty by finding the global maximum of the elongation of the nipple for the specific pressure in the breast shield.

The breast status determination unit can be configured to determine the status of the breast, e.g. to estimate the breast emptiness, based on the local maxima of the elongation of the nipple for the specific pressure in the breast shield. The breast status determination unit can be configured to generate a breast status signal, e.g. a breast emptiness status signal indicating that the breast of the user is empty, if a predetermined condition is fulfilled, e.g., if the elongation of the nipple for the specific pressure in the breast shield reaches a predetermined threshold value, if the change in the maximum of the elongation of the nipple between two consecutive cycles is below a predetermined threshold value for a predetermined number of cycles or a predetermined amount of time. The breast status determination unit can be configured to provide the breast status signal. e.g. the breast emptiness status signal, to the breast status indication unit. The breast status indication unit can be configured to indicate the determined status. e.g. the breast emptiness, to the user based on the breast status signal. Alternatively or additionally the breast status determination unit can be configured to provide the breast status signal, e.g. breast emptiness status signal, to the breast pump control unit. The breast pump control unit can be configured to provide a control signal to the pressure source to end the milk extraction session if the breast status signal. e.g. breast emptiness status signal indicates that the breast of the user is empty or to adjust a pressure generation setting of the pressure source in dependence of the breast status signal. e.g., increasing or decreasing frequency and/or pressure of the cycles of alternating increased pressure and decreased pressure generated by the pressure source. The breast status signal can comprise the adapted breast shield setting used for controlling the pressure generation setting.

The breast pump control unit can alternatively or additionally be configured to provide sampling of the elongation of the nipple with a sampling rate which is at least 3 times higher than a frequency of the cycles of alternating increased pressure and reduced pressure in the breast shield generated by the pressure source. Alternatively or additionally, the nipple elongation measurement unit can be configured to provide sampling of the elongation of the nipple with a sampling rate which is at least 3 times higher than a frequency of the cycles of alternating increased pressure and reduced pressure in the breast shield generated by the pressure source. The nipple elongation measurement unit can be configured to estimate the elongation of the nipple for the specific pressure in the breast shield of each cycle of alternating increased pressure and reduced pressure. e.g. by interpolating the measured sample values. The measured elongation of the nipple can for example be the local maximum if the specific pressure in the breast shield is the maximal reduced pressure in the respective cycle. The nipple elongation measurement unit can be configured to provide the measured elongation of the nipple, e.g. the local maxima of the elongation of the nipple, to the breast status determination unit. The breast status determination unit can be configured to determine the status of the breast of the user, e.g. to estimate breast emptiness, based on the measured elongation of the nipple, e.g. based on the local maxima of the elongation of the nipple.

The breast pump can be configured to use the pressure generation setting adapted for measuring elongation of the nipple in order to perform the sampling of the elongation of the nipple. The pressure generation setting can for example be controlled based on the breast shield setting. The breast pump can for example be configured to use a longer duration at the maximal reduced pressure compared to normal operation during milk extraction sessions or a lower maximal reduced pressure compared to normal operation during milk extraction sessions. This allows a more accurate measurement of the elongation of the nipple for the specific pressure in the breast shield if the maximal reduced pressure is used as specific pressure. In normal operation during milk extraction sessions the reduced pressure for suction present in the breast shield is for example between −50 mbar to −500 mbar for a duration of between 10 ms and 5000 ms. Typically maximal reduced pressure for suction. e.g., the specific pressure in the breast shield, is present in the breast shield for a duration of between 1 ms and 500 ms.

The breast pump can be configured to perform a calibration measurement in order to estimate the maximal elongation of the nipple for the specific pressure in the breast shield that occurs when the breast of the user is empty. The breast pump can be configured to perform a calibration measurement in which milk is extracted from the breast for a duration such that it is ensured that the breast is empty. e.g., for a duration of 30 minutes, 25 minutes, 20 minutes, or 15 minutes. Alternatively or additionally the breast pump can be configured to use one or more previous milk extraction sessions as calibration measurements. The global maximum of the elongation of the nipple for the specific pressure in the breast shield of the calibration measurement or calibration measurements can be used as a measure for subsequent milk extraction session in order to estimate when the breast is empty. This allows a more accurate estimation of the breast emptiness.

Alternatively or additionally the breast emptiness unit can be configured to estimate an amount of milk in the breast of the user at the beginning of the milk extraction session based on a calibration measurement, e.g., by measuring the amount of extracted milk in one or more previous milk extraction sessions and using the measured amount of extracted milk as estimate for the amount of milk in the breast of the user at the beginning of the subsequent milk extraction session. The estimation of the amount of milk in the breast of the user at the beginning of the milk extraction session can for example further be multiplied with a correction factor for increasing or decreasing the estimated amount of milk in the breast of the user in dependence of a milk extraction session history. For example if the milk extraction session history shows a decreasing or increasing amount of milk for each subsequent milk extraction session, the correction factor can be used for decreasing or increasing the estimated amount of milk in the breast of the user at the beginning of the subsequent milk extraction session. Estimating the amount of milk in the breast of the user at the beginning of the milk extraction session allows to indicate breast emptiness during the milk extraction session. The elongation of the nipple for the specific pressure in the breast shield can be correlated to the current amount of milk left in the breast in order to allow to indicate breast emptiness during the milk extraction session.

The breast pump can comprise a breast unit and a base unit. The breast unit can comprise the breast shield. The breast unit can furthermore comprise the breast status determination device or parts of the breast status determination device. The breast unit can be configured to be arranged at the breast of the user. The base unit can comprise the pressure source, a power supply, or the pressure source and the power supply. The power supply is configured for providing power. The breast unit and the base unit can be connected via a connection line. The connection line can comprise an air-duct, a power line, an optical connection, or any combination of them.

The power line can be a power cord connected from the base unit of the breast pump to the breast unit in order to supply power to the breast unit. Alternatively or additionally the breast unit can be powered by the power source of the breast status determination device.

The breast unit can comprise a container for storing extracted milk. The breast unit can comprise a breast shield connector for connecting the breast shield with the container.

The breast status determination device can be connected to or can be part of any suitable breast pump.

In a further aspect of the present invention a use of a measurement of an elongation of a nipple of a breast of a user for a specific suction force applied to the nipple during a milk extraction session is presented. The specific suction force applied to the nipple is generated by providing a specific pressure to the nipple. The measurement is used for determining a status of the breast of the user. The determined status of the breast of the user can be an estimated breast emptiness of the breast of the user, a detected presence or absence of a MER, or the estimated breast emptiness of the breast of the user and the detected presence or absence of the MER of the breast of the user.

In a further aspect of the present invention a method for operating the breast pump according a representative embodiment of the breast pump is presented. The method comprises the steps.

generating cycles of alternating increased pressure and reduced pressure in the breast shield to extract milk from the breast of the user, measuring elongation of the nipple of the breast received in the breast shield for the specific pressure in the breast shield during the milk extraction session, and determining a status of the breast of the user based on the elongation of the nipple of the breast of the user. The determined status of the breast of the user can be an estimated breast emptiness of the breast of the user, a detected presence or absence of a MER, or the estimated breast emptiness of the breast of the user and the detected presence or absence of the MER of the breast of the user.

The method can be a non-therapeutic method. The non-therapeutic method allows to increase the milk extracted by the breast pump as for example a respective milk extraction session can be ended as soon as the breast is empty and the breast pump can be applied without undue delay to extract milk from another breast in a new milk extraction session. The non-therapeutic method can for example be used for operating the breast pump in dairy cattle farming for increasing the milk extracted from dairy cattle by determining the point in time when the breast from which milk is extracted is empty and the breast pump can be applied to the next breast, e.g., of another cow. This allows to reduce the time in which the breast pump tries to extract milk from an already empty breast.

The method can comprise the step:

indicating the determined status of the breast of the user.

Alternatively or additionally, the method can comprise the step:

indicating when the breast of the user is empty.

The method can comprise the step:

measuring the pressure in the breast shield in order to determine when the specific pressure is provided in the breast shield.

The method can comprise the step:

recording images of the nipple of the breast of the user during the milk extraction session. The elongation of the nipple of the breast of the user for the specific pressure in the breast shield during the milk extraction session is measured based on the recorded images.

Alternatively or additionally, the method can comprise the step:

measuring a distance between a tip of the nipple of the breast of the user and a fixed point arranged opposite of the tip and axially aligned to the direction in which the nipple elongates during the milk extraction session. The elongation of the nipple of the breast of the user for the specific pressure in the breast shield during the milk extraction session is measured based on the measured distance between the tip of the nipple and the fixed point during the milk extraction session. The distance can for example be measured based on changes of an electromagnetic field or based on time of flight of a signal such as ultrasound or an infrared signal during the milk extraction session.

Alternatively or additionally the method can comprise the step:

estimating a pressure drop within the breast shield in which the breast of the user is received during the milk extraction session. The elongation of the nipple of the breast of the user for the specific pressure in the breast shield during the milk extraction session is measured based on the estimated pressure drop within the breast shield.

Alternatively or additionally the method can comprise the step:

measuring a shape of the nipple during the milk extraction session. The elongation of the nipple of the breast of the user for the specific pressure in the breast shield during the milk extraction session is measured based on the measured shape of the nipple for the specific pressure in the breast shield during the milk extraction session. Measuring the shape of the nipple can for example be performed by measuring a shape of a collapsible membrane conforming to the shape of the breast during the milk extraction session. The shape of the collapsible membrane can for example be measured by measuring strain at various positions on the collapsible membrane and deriving a local curvature of the part of the collapsible membrane in physical contact with the nipple during the milk extraction session in order to measure the elongation of the nipple for the specific pressure in the breast shield during the milk extraction session. Based on the local curvature the shape of the collapsible membrane can be measured during the milk extraction session. From the shape of the collapsible membrane, the shape of the nipple can be derived, which can be used to measure the elongation of the nipple for the specific pressure in the breast shield during the milk extraction session. Alternatively or additionally measuring the shape of the nipple during the milk extraction session can be performed based on measurements performed by an accelerometer for estimating the shape of the collapsible membrane.

The method can comprise the step:

measuring a shape of the breast during the milk extraction session in order to improve estimation of breast emptiness. Measuring the shape of the breast can for example be performed by measuring a shape of a collapsible membrane enclosing the breast and conforming to the shape of the breast during the milk extraction session. The shape can for example be measured by measuring strain at various positions on the collapsible membrane and deriving a local curvature of the collapsible membrane at the positions. Based on the local curvature the shape of the collapsible membrane can be measured during the milk extraction session. The shape of the collapsible membrane can be used to provide additional information for estimating the breast emptiness of the breast of the user.

In a further aspect of the present invention a computer program for operating a breast pump according to a representative embodiment of the breast pump is presented. The computer program comprises program code means for causing a processor to carry out the method of a representative embodiment of the method, when the computer program is run on the processor.

In a further aspect, a computer readable medium having stored the computer program of a representative embodiment is presented. Alternatively or additionally, the computer readable medium can have the computer program according to any embodiment of the computer program stored.

It shall be understood that the breast status determination device of representative embodiment, the breast pump of representative embodiment, the method of representative embodiment, the computer program of representative embodiment, and the computer readable medium of representative embodiment have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
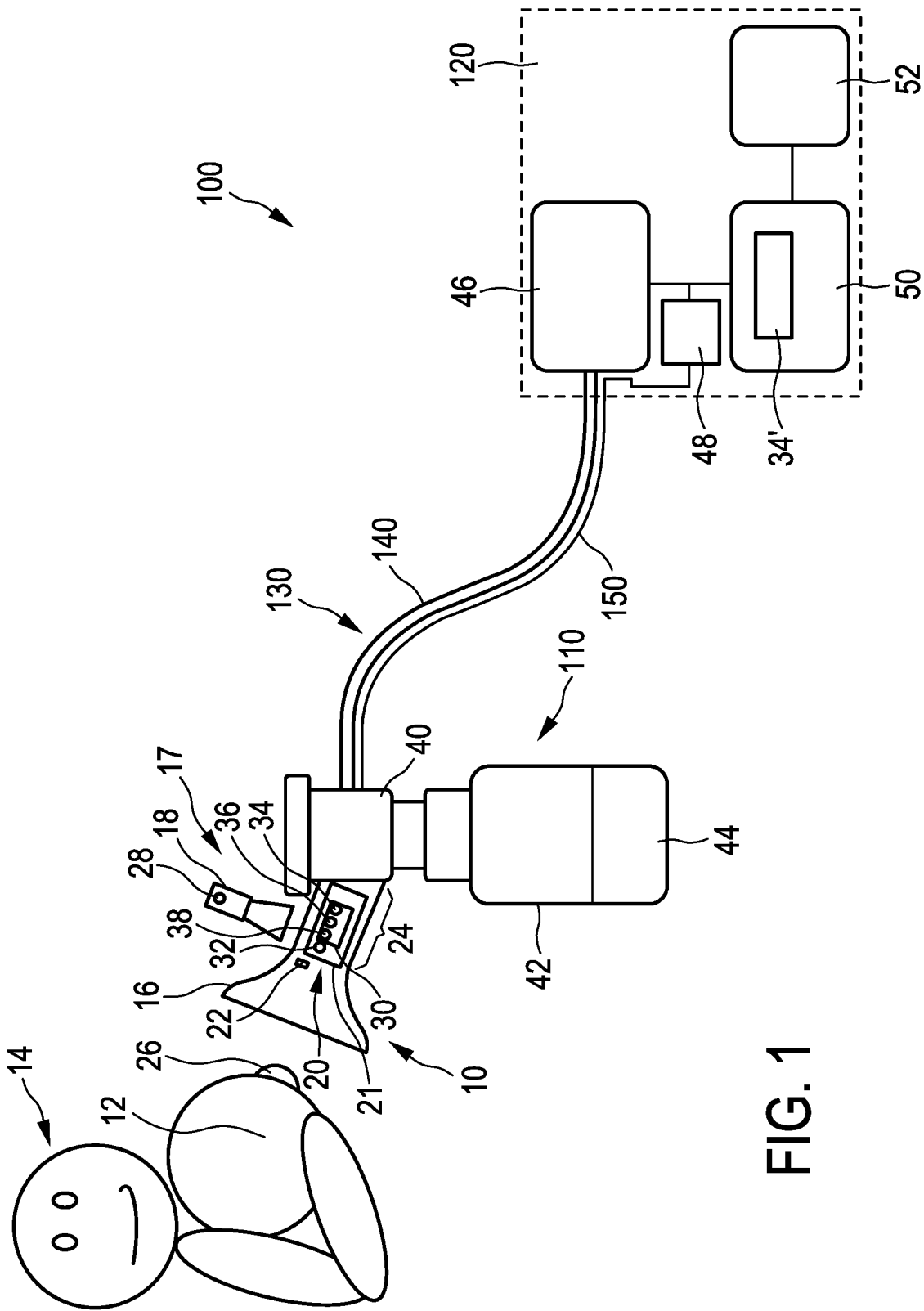
FIG. 1 shows schematically and exemplarily a first embodiment of a breast status determination device in a first embodiment of a breast pump.

FIG. 1 shows schematically and exemplarily a first embodiment of a breast status determination device 10 in a first embodiment of a breast pump 100. The breast status determination device 10 can be used for estimating breast emptiness. i.e. an amount of milk left in a breast 12 of a user 14. In other embodiments the breast status determination device can be configured for detecting a presence or absence of a MER or for estimating the breast emptiness and for detecting the presence or absence of the MER. The breast pump 100 can be used for extracting milk from the breast 12 of the user 14. The breast pump 100 comprises a breast unit 110 and a base unit 120. The breast unit 110 and the base unit 120 are connected via connection line 130. The breast unit 110 comprises the breast status determination device 10 and can be arranged at the breast 12 of the user 14.

The breast status determination device 10 comprises a breast shield 16, a nipple elongation measurement unit 17 in form of a camera 18, a breast status determination unit 20 comprising a breast emptiness estimation unit 21, and a breast status indication unit in form of an alarm 22. In other embodiments the nipple elongation measurement unit can for example be a distance sensor, a pressure estimation unit, or a nipple shape measurement unit. In yet other embodiments the nipple elongation measurement unit can include camera, distance sensor, pressure estimation unit, nipple shape measurement unit, or any combination of them. The camera, distance sensor, and pressure estimation unit allow to measure the elongation of a nipple of the breast of the user for a specific pressure in the breast shield based on an indirect measurement, i.e., without physical contact to the nipple. The pressure estimation unit can furthermore be used to measure the specific pressure in the breast shield. In other embodiments the breast status indication unit can additionally or alternatively comprise a MER detection unit for detecting a presence or absence of a MER.

The breast shield 16 is funnel shaped for comfortably receiving the breast 12 therein and has a nipple tunnel 24 for receiving nipple 26 of the breast 12. The breast shield 16 in this embodiment is made from polyurethane. In other embodiments the breast shield can have any other shape that allows to receive the breast and furthermore can also be made from any other resilient material. e.g. from silicone.

The camera 18 is arranged such that it can record images of the nipple 26 when the breast 12 is arranged in the breast shield 16. The breast shield 16 is translucent in order to allow the camera 18 to record images from the nipple 26. In other embodiments the camera can be arranged directly at the breast shield. e.g., incorporated in the breast shield (cf FIG. 3 and FIG. 6). In further embodiments the camera can be detachable from the breast shield.

Figure 2A:
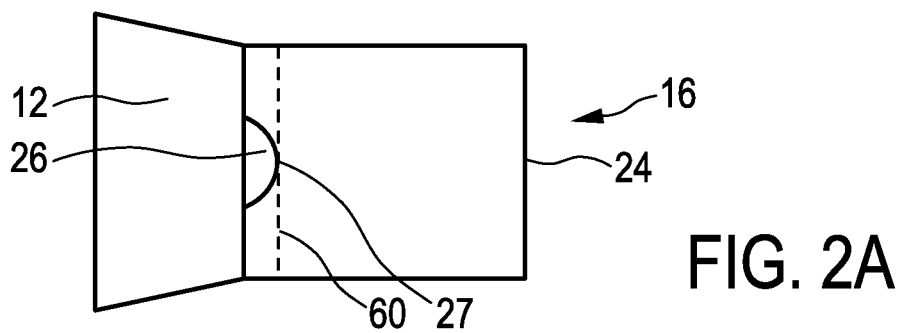
FIG. 2A shows schematically and exemplarily a breast shield of the breast status determination device with a breast arranged in the breast shield and minimal elongation of a nipple for a specific pressure in the breast shield at the beginning of the milk extraction session.

FIGS. 2A. 2B, and 2C show diagrammatically and exemplarily how the recorded images of the nipple 26 in the nipple tunnel 24 look like.

The camera 18 processes the recorded images by measuring the elongation of the nipple 26 over time and measures maximal elongation of the nipple 26 for a maximal reduced pressure in the breast shield 16 during each suction and release cycle, i.e. the camera 18 provides measured local maxima of the elongation of the nipple 26 for the maximal reduced pressure in the breast shield 16. In other embodiments the elongation of the nipple can be measured for another specific pressure. The camera 18 includes an antenna 28 in this embodiment that transmits the local maxima of the elongation of the nipple 26 to the breast emptiness estimation unit 21.

The breast emptiness estimation unit 21 comprises a control unit 30 and an antenna 32. The control unit includes a processor 34, a memory 36, and a sensor in form of a proximity sensor 38. In other embodiments the sensor can also for example be a temperature sensor or any other sensor that allows to detect whether a breast is received in the breast shield. The control unit 30 controls the operation of the breast status determination device 10 and in particular of the breast emptiness estimation unit 21 and the nipple elongation measurement unit 17 in form of the camera 18.

Antenna 32 receives signals from the camera 18. The signals include information regarding the local maxima of the elongation of the nipple 26.

The processor 34 processes the signals received via the antenna 32 from the camera 18. Furthermore the processor can receive control signals from the memory 36 or from the proximity sensor 38. Control signals can for example include sensor data or can be simple control signals for activating or deactivating the camera 18 or the alarm 22.

The memory 36 stores breast shield settings, pressure generation settings, operation modes, and a computer program for operating the breast status determination device 10.

The proximity sensor 38 detects when the breast 12 of the user 14 is received in the breast shield 16 and provides a control signal for activating the camera 18 via antenna 32 to the camera 18. The proximity sensor 38 is optional. In other embodiments the breast status determination device does not include a sensor and the nipple elongation measurement unit can be manually activated.

In other embodiments the control unit deactivates the breast status determination device when the breast of the user is removed from the breast shield. The control unit can also deactivate the breast status determination device when a control signal for deactivating the breast status determination device is received. e.g., provided via user interface.

The control unit 30 allows to operate the breast status determination device 10 such that the camera 18 is automatically activated when the breast is received in the breast shield 16. The control unit 30 in this embodiment deactivates the camera 18 when the breast emptiness estimation unit 21 detects that the breast 12 is empty.

In this embodiment the breast emptiness estimation unit 21 estimates the breast emptiness based on the local maxima of the elongation of the nipple 26 for the maximal reduced pressure in the breast shield 16. In other embodiments the breast emptiness estimation unit can estimate the breast emptiness based on measured elongations of the nipple for another specific pressure in the breast shield. The breast emptiness estimation unit 21 generates a breast emptiness status signal indicating that the breast 12 of the user 14 is empty if a predetermined condition is fulfilled. In this embodiment the condition is that the elongation of the nipple 26 for the maximal reduced pressure in the breast shield 16 reaches a predetermined threshold value. The predetermined threshold value is specific to the user 14 and can for example be derived in a calibration measurement. In the calibration measurement the maximal elongation of the nipple of the breast of the user for the maximal reduced pressure in the breast shield during the milk extraction session can be measured for the empty breast and the maximal elongation of the nipple for the maximal reduced pressure in the breast shield can be set as predetermined threshold value. Alternatively the maximal elongation for another specific pressure in the breast shield can be measured for the empty breast and set as predetermined threshold value if the maximal elongation of the nipple during the milk extraction session is compared to the predetermined threshold value for the specific pressure. The predetermined threshold value can also be slightly below the maximal elongation of the nipple, e.g. 0.1 mm, 0.2 mm, 0.3, mm, 0.4 mm, or 0.5 mm below the maximal elongation of the nipple in order to avoid that the empty breast is not detected. The maximal elongation of the nipple of the breast of the user can also be derived from previous milk extraction sessions. In other embodiments the predetermined condition can for example be that a change in the maximal elongation of the nipple for a specific pressure in the breast shield during the milk extraction session between two consecutive cycles of alternating increased pressure and reduced pressure with milk flow is below a predetermined threshold value, e.g. 0.5 mm.

The breast emptiness estimation unit 21 provides the breast emptiness status signal to the alarm 22. The alarm 22 indicates the breast emptiness to the user based on the breast emptiness status signal by providing a specific alarm sound.

In this embodiment the connection line 130 includes an air-duct 140 and a power line in form of power cord 150. The power cord 150 provides power to the breast emptiness estimation unit 21 and the alarm 22. In other embodiments the power line can additionally provide the nipple elongation measurement unit with power. In yet other embodiments the nipple elongation measurement unit, the breast emptiness estimation unit, and/or the breast status indication unit can be provided with power from a power source arranged at the breast unit. The power line can also be used to transmit data, e.g., control signals.

The breast status determination device 10 is connected with the connection line 130 via breast shield connector 40.

The breast shield connector 40 comprises milk storage container 42 for storing extracted milk 44. In this embodiment the user 14 removed breast 12 from the breast shield 16 ending the milk extraction session. The extracted milk 44 extracted during the milk extraction session is stored in the milk storage container 42.

The breast shield connector 40 and milk storage container 42 together with the breast status determination device 10 form the breast unit 110.

The base unit 120 comprises a pressure source in form of a vacuum pump 46, a power supply 48, a breast pump control unit 50, and a user interface in form of an on and off switch. In other embodiments the user interface can also for example be a touch display, a simple switch, button or any other user interface that allows the user to interact with the breast pump.

The vacuum pump 46 is in air-ducting connection via the air-duct 140 to the breast shield 16 for generating cycles of alternating increased pressure and reduced pressure in the breast shield 16 to extract milk from the breast 12 of the user 14. This allows to generate a suckling pattern with alternating suction and release cycles. Typical suction and release cycles last between 0.5 s to 2 s. e.g., 0.6 s, 1.25 s, or 1.32 s such that 30 to 120 suction and release cycles are generated per minute. In other embodiments, the vacuum pump can be replaced by any other pressure source that allows generating cycles of alternating increased pressure and reduced pressure. The vacuum pump can for example be replaced by a manual vacuum pump that is operated with a handle. Such a manual vacuum pump can for example be included in the breast unit. This allows improved mobile operation.

The power supply 48 provides power to the components of the base unit 120 and via the power cord 150 also to the components of the breast unit 110.

The breast pump control unit 50 comprises a processor 34'. The breast pump control unit 50 controls the operation of the vacuum pump 46 and the power supply 48. This allows operating the breast pump 100. The breast pump control unit 50 has an antenna for communicating with the breast emptiness estimation unit 21 and the camera 18 (not shown). The antenna is optional. Alternatively the breast pump control unit 50 can also be connected to the breast status determination unit and/or the nipple elongation measurement unit via a wired connection, e.g. via the connection line. In other embodiments the breast pump control unit can also be used for controlling the breast status determination device. Tis allows central control of the breast pump and all of its components.

The breast pump control unit 50 provides that sampling of the elongation of the nipple 26 is performed with a sampling rate which is at least 3 times higher than a frequency of the cycles of alternating increased pressure and reduced pressure in the breast shield 16 generated by the vacuum pump 46 in this embodiment. In other embodiments, the breast pump control unit can synchronize a moment of sampling of the elongation of the nipple with a specific pressure, e.g. the maximal reduced pressure, in the breast shield generated by the pressure source.

In other embodiments, the breast pump can be used with a pressure generation setting adapted for measuring elongation of the nipple in order to perform the sampling of the elongation of the nipple. The breast pump can for example be used with a longer duration at the maximal reduced pressure compared to normal operation during milk extraction sessions or a lower maximal reduced pressure compared to normal operation during milk extraction sessions. The lower maximal reduced pressure applies a higher suction force on the nipple of the breast of the user. This allows a more accurate measurement of the elongation of the nipple for the specific pressure in the breast shield if the maximal reduced pressure is used as specific pressure. In normal operation during milk extraction sessions the reduced pressure for suction present in the breast shield is for example between −50 mbar to −500 mbar for a duration of between 10 ms and 5000 ms, e.g. between 500 ms and 2000 ms. Typically maximal reduced pressure for suction, e.g., the specific pressure in the breast shield, is present in the breast shield for a duration of between 1 ms and 500 ms.

The breast pump can furthermore be used to perform a calibration measurement in order to estimate the maximal elongation of the nipple for the maximal reduced pressure that occurs when the breast of the user is empty. In other embodiments another specific pressure can be used in the calibration measurement. The maximal elongation of the nipple of previous milk extraction sessions can be recorded and the maximal elongation of the nipple of previous milk extraction sessions can for example be used as maximal elongation of the nipple corresponding to the elongation for which the breast is defined to be empty.

The measurement of the elongation of the nipple of the breast of the user during the milk extraction session can be used for estimating the breast emptiness of the breast of the user. This allows to estimate when the breast of the user is empty and when the user can end the milk extraction session without additional risk of mastitis caused by milk left in the breast.

Figure 2B:
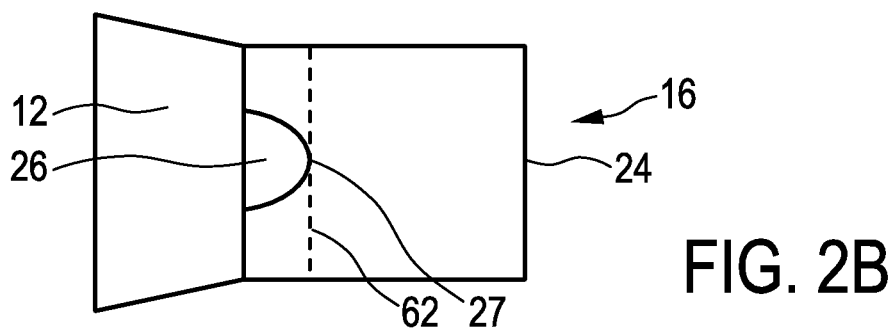
FIG. 2B shows intermediate elongation of the nipple for the specific pressure in the breast shield in the milk extraction session.
Figure 2C:
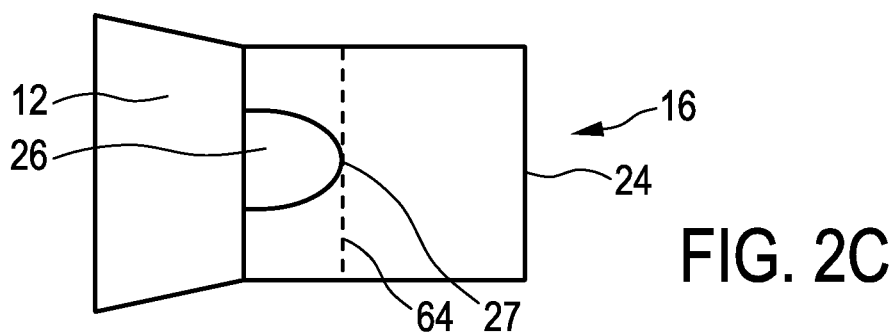
FIG. 2C shows maximal elongation of the nipple for the specific pressure in the breast shield at the end of the milk extraction session.

FIG. 2A to FIG. 2C schematically and exemplarily show recorded images of the nipple 26 in the nipple tunnel 24 of the breast shield 16 of the breast status, which is illustratively funnel-shaped, breast status determination device 10 presented in FIG. 1 for the same maximal reduced pressure in the breast shield 16 in each of the three recorded images. Other images with different elongation of the nipple can be recorded for other specific pressure (not shown).

Figure 2D:
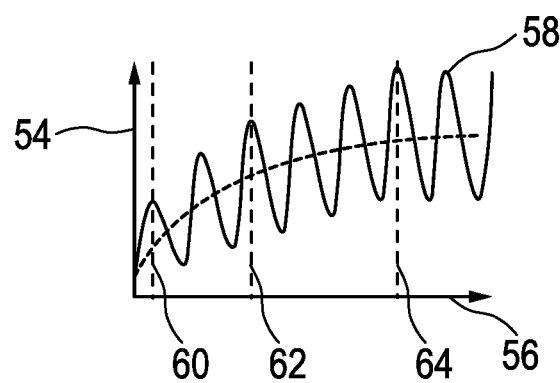
FIG. 2D shows diagrammatically and exemplarily elongation of the nipple over time during the milk extraction session.

FIG. 2D schematically and exemplarily shows elongation 54 of the nipple 26 over time 56. Maxima 58 of the elongation 54 of the nipple 26 increase over time 56. The maxima 58 of the elongation 54 of the nipple 26 shown in the graph of FIG. 2D are elongations 54 of the nipple 26 for the same maximal reduced pressure in the breast shield 16. The elongation 54 of the nipple 26 follows the suction and release pattern induced by the cycle of alternating increased pressure and reduced pressure. When suction is increased. i.e. pressure is reduced, the elongation 54 of the nipple 26 increases until a maximum is reached for maximal reduced pressure. When suction is reduced. i.e., pressure is increased, during periods of release, the elongation 54 of the nipple 26 decreases again. The minima of elongation 54 depend on the suction pattern performed on the nipple 26. e.g., whether there is enough time for relaxation and/or whether there is a baseline suction, e.g., increased pressure below 1 bar. In this embodiment there is an increasing baseline suction. i.e., during release the increased pressure in the breast shield 16 is higher than the maximal reduced pressure but below a pressure surrounding the breast shield 16 and the increased pressure is reduced over the number of suction and release cycles in order to increase the baseline suction over time. Furthermore no cycles without milk flow are shown in the graph of FIG. 2D.

Typically, a milk extraction session takes about 15 minutes per breast and typically 30 to 120 suction and release cycles are performed per minute. FIG. 2D shows a much smaller frequency which does not correspond to an actual breast pump frequency that would be used. FIG. 2D is for illustrative purposes and illustrates that the elongation 54 of the nipple 26 cyclically increases over time and that the maxima 60, 62, 64 of the elongation of the nipple 26 for maximal reduced pressure in the breast shield 16 increase over time as long as milk is extracted from breast 12.

FIG. 2A shows a tip 27 of the nipple 26 in a position that corresponds to the local maximum 60 of the elongation 54 of the nipple 26 for maximal reduced pressure in the breast shield 16 after about a half second of the milk extraction session.

FIG. 2B shows an intermediate elongation of the nipple 26 at the local maximum 62 of the elongation 54 of the nipple 26 for maximal reduced pressure in the breast shield 16 after about 5 minutes of the milk extraction session.

FIG. 2C shows maximal elongation of the nipple 26 with the maximum 64 of the elongation 54 of the nipple 26 for maximal reduced pressure in the breast shield 16 at the end of the milk extraction session. In this case the milk extraction session took 12.5 minutes. The maximum 64 of the elongation of the nipple for the maximal reduced pressure in the breast shield 16 reached the predetermined threshold value corresponding to the empty breast. Thus, the breast 12 is determined to be empty and the milk extraction session is ended. In another embodiment the milk extraction session could have been ended based on the condition that the maxima of the elongation of the nipple 26 following the maximum 64 of the elongation 54 of the nipple 26 are unchanged, e.g., below a threshold value of 0.5 mm, for the maximal reduced pressure in the breast shield 16 for a predetermined number of maxima, a predetermined duration, or during presence of the MER.

Figure 3:
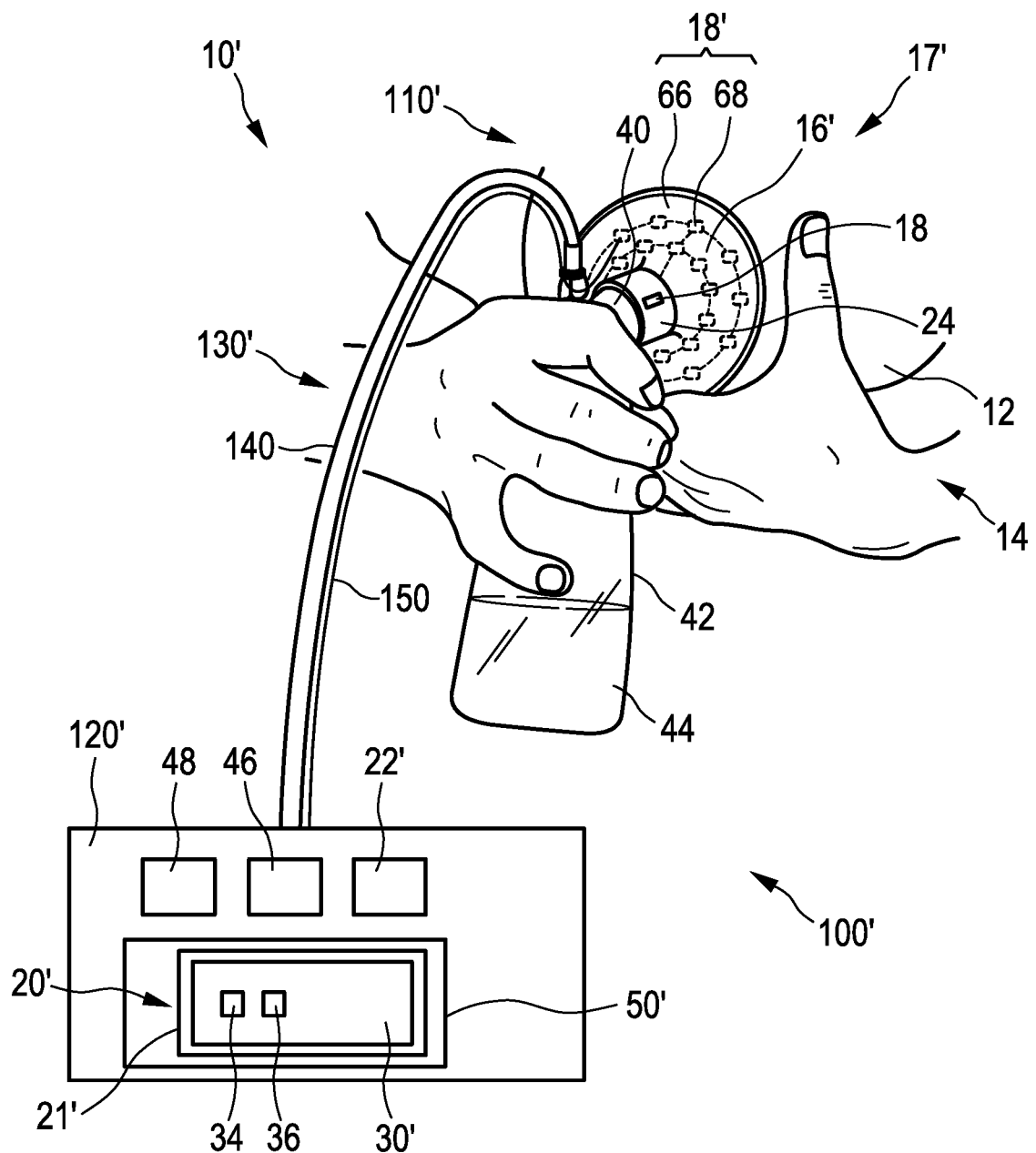
FIG. 3 shows schematically and exemplarily a second embodiment of the breast status determination device in a second embodiment of the breast pump.

FIG. 3 shows schematically and exemplarily a second embodiment of the breast status determination device 10' in a second embodiment of the breast pump 100'. The breast pump 100' comprises breast unit 110' and base unit 120' which are connected via connection line 130'. The connection line 130' comprises air-duct 140 and a power and data line in form of power cord 150. The breast unit 110' is arranged at breast 12 of user 14. The breast unit 110' comprises a part of the breast status determination device 10', a breast shield connector 40, and a milk storage container 42.

The breast status determination device 10' includes a breast shield 16', a nipple elongation estimation unit 17' including camera 18 and a nipple shape measurement unit 18'. The nipple shape measurement unit 18' includes a collapsible membrane 66 and a membrane shape measurement unit in form of strain sensors 68. The breast status determination device 10' furthermore comprises a breast status determination unit 20' comprising a breast emptiness estimation unit 21' arranged in the base unit 120'. In other embodiments the breast emptiness estimation unit can be arranged in the breast unit. Only one of the camera 18 and the nipple shape measurement unit 18' is required in order to measure the elongation of the nipple. Using both the camera 18 and the nipple shape measurement unit 18' for measuring the elongation of the nipple allows to increase the accuracy of the measurement. In other embodiments the strain sensors can be replaced by an accelerometer or any other membrane shape measurement unit that allows to measure a shape of the collapsible membrane during a milk extraction session.

The breast shield 16' has a nipple tunnel 24 in which the nipple of the breast 12 of the user 14 is arranged during the milk extraction session. In the breast shield 16' increased pressure and reduced pressure is provided to extract milk from the breast 12 of the user 14. Extracted milk 44 is stored in the milk storage container 42. The increased pressure and reduced pressure is provided via the air-duct 140 and the breast shield connector 40 from the base unit 120'. The breast shield 16' is funnel shaped and made from pol urethane. In other embodiments the breast shield can have a different shape and can also be made from a different resilient material, e.g. from silicone. The collapsible membrane 66 and the strain sensors 68 of the nipple shape measurement unit 18' are incorporated in the breast shield 16'. The camera 18 is also incorporated in the breast shield 16'. The camera 18 is arranged at the nipple tunnel 24 and records images during the milk extraction session. The recorded images are transmitted to the base unit 120' via power cord 150.

The collapsible membrane 66 encloses the breast 12 of the user 14 when the breast 12 is received in the breast shield 16' The collapsible membrane 66 has a small opening that allows extracted milk 44 to pass from the nipple through the nipple tunnel 24 and the breast shield connector 40 into the milk storage container 42. In other embodiments the collapsible membrane can also be formed such that an opening is generated that allows milk to pass (not shown). The collapsible membrane 66 can contract and expand in dependence of a shape of the breast 12 of the user 14, i.e., the collapsible membrane 66 can have an unextended state, extend to an extended state, and reduce its size again in order to contract to the unextended state. The collapsible membrane 66 provides that the shape of the collapsible membrane 66 conforms to the shape of the breast 12 of the user 14 during the milk extraction session. In this embodiment the collapsible membrane 66 is made from a reversibly deformable material, such as silicone elastomer, latex material, or rubber. In the unextended state, the collapsible membrane 66 covers an area that is smaller than the surface area of the breast 12 of the user 14 in an empty state, i.e., the surface area covered by the collapsible membrane 66 in the unextended state is smaller than the surface area of the empty breast. When the breast 12 is inserted into the breast shield 16' and therefore also into the collapsible membrane 66, the collapsible membrane 66 is extended into the extended state that allows the collapsible membrane 66 to conform to the shape of the breast 12. During the milk extraction session, milk is extracted from the breast 12 and the size and therefore also the surface area of the breast 12 is reduced. The collapsible membrane 66 conforms to the shape of the breast 12 during the milk extraction session by reducing the area covered. The collapsible membrane 66 can therefore conform to the shape of the breast 12 during the milk extraction session by reducing the size of the collapsible membrane 66 when milk is extracted from the breast 12 until the end of the milk extraction session.

The strain sensors 68 are distributed over the surface of the collapsible membrane 66 at various positions on the collapsible membrane 66. The strain sensors 68 measure the shape of the collapsible membrane 66 during the milk extraction session in order to improve estimation of breast emptiness. In particular a part of the collapsible membrane 66 is in physical contact with the nipple and some of the strain sensors 68 are arranged around the nipple in this embodiment (not shown). The strain sensors 68 measure local strain which corresponds to a local curvature. The shape of the collapsible membrane 66 that corresponds to the shape of the breast 12 can be estimated based on data of the strain sensors 68. The shape of the nipple can also be measured based on the local curvature measured based on the data of the strain sensors 68 arranged around the nipple. This allows to measure the elongation of the nipple, as the elongation of the nipple depends on the shape of the nipple. Furthermore the shape of the breast 12 and the amount of milk remaining in the breast 12 are correlated. This allows to provide additional information in order to estimate breast emptiness. The strain sensors 68 are connected via the power cord 150 to the base unit 120' This allows to transmit signals from the nipple shape measurement unit 18' via the power cord 150 to the base unit 120'.

In other embodiments the collapsible membrane can also be pressing on the nipple and/or the breast to a certain extend in order to perform a peristaltic action or a massaging action on the nipple and/or breast for stimulating the MER and/or for supporting the extraction of milk from the nipple. Such a collapsible membrane is for example disclosed in WO 2010/109398 A1 which is incorporated herein by reference. The membrane shape measurement unit can be configured to correct the additional deformation caused by the pressure on the nipple and/or breast in order to measure the elongation of the nipple for a specific pressure in the breast shield. Alternatively the membrane shape measurement unit can also be configured to use the pressing on the nipple and/or breast for obtaining information on the stiffness of the nipple and/or breast.

In yet other embodiments a baseline suction can be provided in the breast shield in order to ensure that the collapsible membrane conforms to the shape of the breast during the whole milk extraction session. The collapsible membrane is then continuously in contact with the breast and the nipple. The membrane shape measurement unit can be configured to measure the shape of the nipple when the collapsible membrane is not used for peristaltic action or massaging action, e.g., during increased pressure in form of baseline suction.

The base unit 120' comprises a breast pump control unit 50', a vacuum pump 46, a power supply 48, and a breast status indication unit in form of an automatic switch-off unit 22'. In other embodiments the automatic switch-off unit can also be part of the breast pump control unit 50'. In yet other embodiments the automatic switch-off unit can be replaced by any other breast status indication unit, e.g. a visual indication unit, an audio indication unit, or any other type of breast status indication unit, such as a haptic indication unit.

The breast pump control unit 50' comprises the breast emptiness estimation unit 21'. The breast emptiness estimation unit 21' comprises a control unit 30'. The control unit 30' comprises a processor 34 and a memory 36.

The processor 34 processes the signals received via power cord 150 from the camera 18 and the nipple shape measurement unit 18'. Furthermore the processor can receive control signals from the memory 36.

The memory 36 stores breast shield settings, pressure generation settings, operation modes, and a computer program for operating the breast status determination device 10'. The memory furthermore stores a table with values of breast emptiness in dependence of elongations of the nipple and specific pressure in the breast shield 16' The values of breast emptiness in dependence of elongations of the nipple and specific pressure in the breast shield 16' are recorded in previous milk extraction sessions in order to use them in subsequent milk extraction sessions. The stored table is used to provide the breast emptiness corresponding to the measured elongation of the nipple for a specific pressure in the breast shield 16'. If a measured elongation of the nipple and/or a pressure in the breast shield 16' are between two stored values, an interpolated breast emptiness can be provided. Furthermore the memory 36 stores a milk extraction session history with amount of milk extracted in previous milk extraction sessions and the according time of the milk extraction sessions. This allows to provide an estimated amount of milk in the breast 12 at the beginning of the milk extraction session. When breast emptiness below a predetermined threshold value is detected, in this embodiment below 1% amount of milk left in the breast 12 of the user 14 compared to the amount of milk in the breast 12 at the beginning of the milk extraction session, the breast emptiness estimation unit 21' generates abreast emptiness status signal that is provided to the automatic switch-off unit 22'. The automatic switch-off unit 22' ends the milk extraction session by automatically turning of the breast pump 100'.

In other embodiments the memory additionally or alternatively stores a breast emptiness estimation function with the elongation of the nipple and specific pressure in the breast shield as input and breast emptiness as output. The values of breast emptiness in dependence of elongations of the nipple and specific pressure in the breast shield recorded in previous milk extraction sessions can be used as training data for determining coefficients for the breast emptiness estimation function based on machine learning, regression analysis, or any other method for deriving coefficients based on training data.

The breast pump control unit 50' controls the operation of the breast pump 100'. The breast pump control unit 50' controls the suction pattern provided by the vacuum pump 46, power provided by the power supply 48, and the nipple elongation estimation unit 17' including the camera 11 and the nipple shape measurement unit 18'.

The vacuum pump 46 generates cycles of alternating increased pressure and reduced pressure and applies the increased pressure and reduced pressure via the air-duct 140 and breast shield connector 40 to the breast shield 16'. In other embodiments the vacuum pump can be replaced by any other pressure source, e.g. a manual handle for applying increased pressure and reduced pressure to the breast shield.

The power supply 48 provides power to the components of the base unit 120' and to the breast unit 110' via the power cord 150.

The operation of the breast pump 100' presented in FIG. 3 is similar to the operation of the breast pump 100 presented in FIG. 1. Breast pump 100' and breast pump 100 both estimate breast emptiness using recorded images of cameras. However, breast pump 100' and breast pump 100 are different in that breast pump 100' additionally measures the elongation of the nipple for the specific pressure in the breast shield 16' using the nipple shape measurement unit 18'. Therefore an average value can be calculated from the two different ways of measuring the elongation of the nipple for the specific pressure in the breast shield 16'. Furthermore estimating the breast emptiness is performed in breast pump 100' based on the table of values of breast emptiness in dependence of elongations of the nipple and specific pressures in the breast shield 16'. Additionally breast pump 100' is automatically switched off when the amount of milk left in the breast 12 is below 1% of the estimated amount of milk at the beginning of the milk extraction session.

Figure 4:
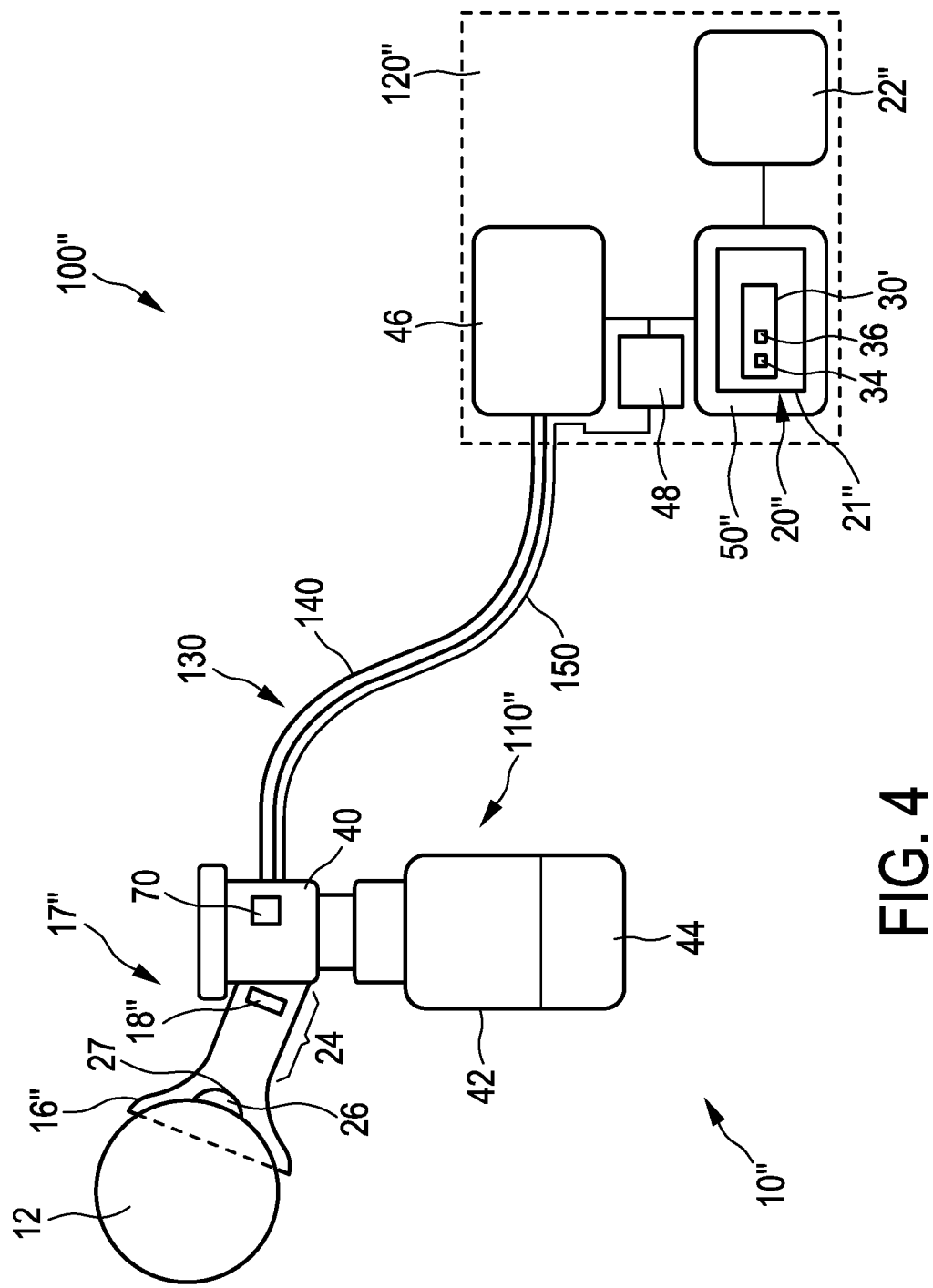
FIG. 4 shows schematically and exemplarily a third embodiment of the breast status determination device in a third embodiment of the breast pump.

FIG. 4 shows schematically and exemplarily a third embodiment of the breast status determination device 10" in a third embodiment of the breast pump 100".

The breast pump 100" comprises a breast unit 110" and a base unit 120". The breast unit 110" can be arranged at a breast 12. The breast unit 110" and the base unit 120" are connected via connection line 130. In this embodiment the connection line 130 includes an air-duct 140 and a power and data line in form of power cord 150.

The breast status determination device 10" comprises a breast shield 16", a nipple elongation measurement unit 17" including a distance sensor in form of an ultrasound sensor 18", a battery 70, a breast status determination unit 20" comprising a breast emptiness estimation unit 21", and a breast status indication unit in form of a display 22".

The breast shield 16" has a nipple tunnel 24 in which the ultrasound sensor 18" is arranged FIG. 4 shows the breast 12 moving away from the breast shield 16" after the end of a milk extraction session. Breast shield connector 40 includes milk storage container 42 for storing extracted milk 44. During the milk extraction session, nipple 26 of the breast 12 is arranged in the nipple tunnel 24.

The ultrasound sensor 18" is arranged opposite of a tip 27 of the nipple 26 of the breast 12 and axially aligned to the direction in which the nipple 26 elongates during the milk extraction session. The ultrasound sensor 18" measures a time of flight of ultrasound between the ultrasound sensor 18" and the tip 27 of the nipple 26 of the breast 12 during the milk extraction session in order to measure the elongation of the nipple 26 for a specific pressure in the breast shield 16". In other embodiments the ultrasound sensor can be replaced by another distance sensor, e.g., an acoustic distance sensor or an optical distance sensor in order to measure the distance between the tip of the nipple of the breast of the user and the distance sensor. The ultrasound sensor can also be replaced by a proximity sensor, such as a radar, a sonar, or the like. In other embodiments the distance between the distance sensor and the tip of the nipple of the breast of the user can also be measured based on changes of an electromagnetic field or time of flight measurements of a signal, such as an infrared signal.

The measured elongation of the nipple 26 is provided to the base unit 120" via the power cord 150 from the ultrasound sensor 18".

In this embodiment battery 70 powers ultrasound sensor 18". Battery 70 is optional. The battery 70 is rechargeable and can be charged via the power cord 150.

The base unit 120" comprises a breast pump control unit 50", a vacuum pump 46, a power supply 48, and the display 22".

The breast emptiness estimation unit 21" comprises control unit 30" with processor 34 and memory 36. The breast emptiness estimation unit 21" uses a breast emptiness estimation function with the elongation of the nipple for a maximal reduced pressure as input and breast emptiness as output. In other embodiments the breast estimation unit can also use other methods for estimating the breast emptiness. e.g. using another specific pressure in the breast shield or a method based on a table with values of breast emptiness in dependence of elongations of the nipple and specific pressure in the breast shield or estimating when the breast is empty by comparing the elongation of the nipple for a specific pressure in the breast shield for consecutive cycles of alternating increased pressure and reduced pressure.

The display 22" provides a graphical representation of the breast emptiness over time estimated based on the breast emptiness function. This allows the user to decide when to end the milk extraction session.

Figure 5:
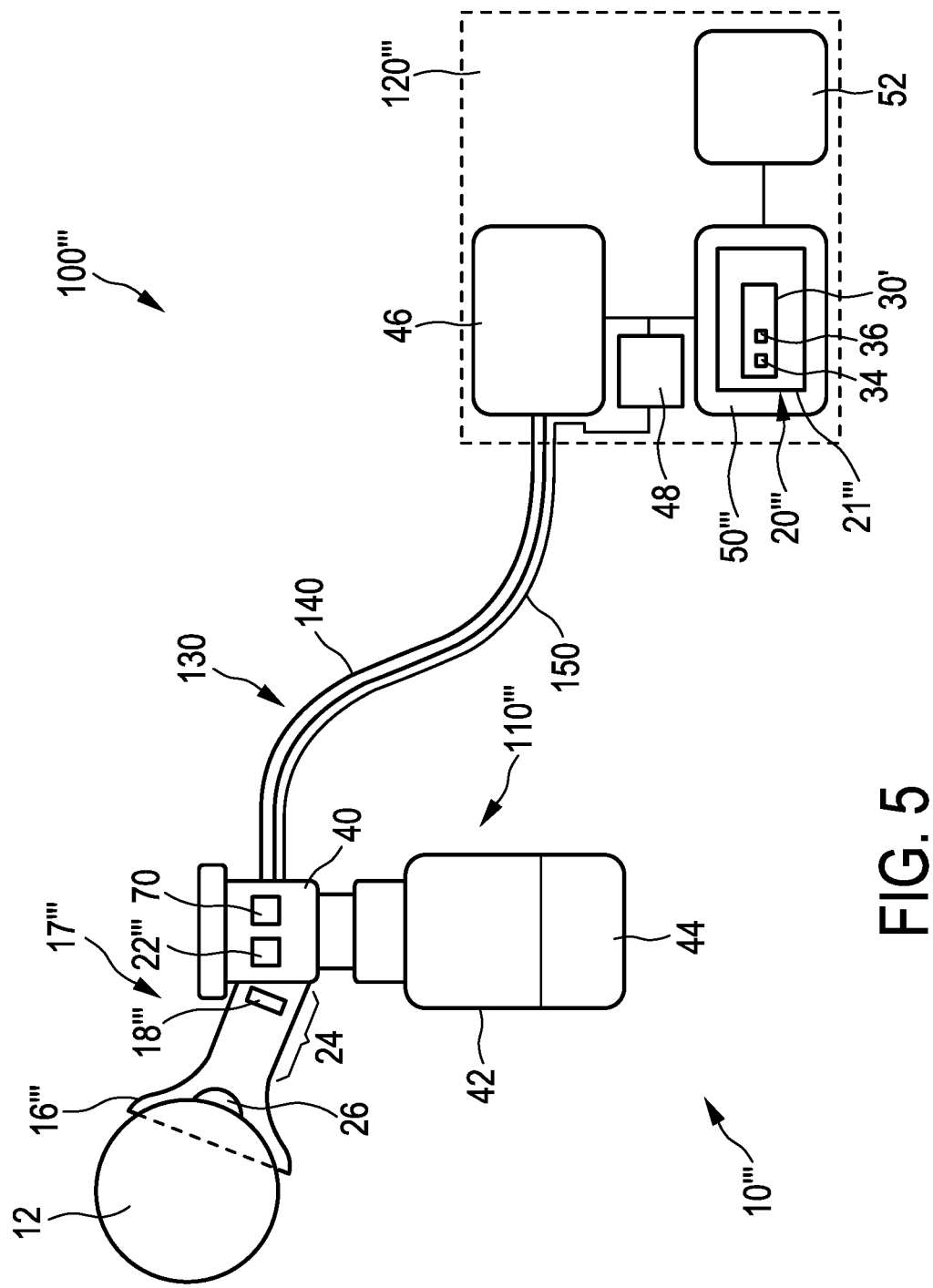
FIG. 5 shows schematically and exemplarily a fourth embodiment of the breast status determination device in a fourth embodiment of the breast pump.

FIG. 5 shows schematically and exemplarily a fourth embodiment of the breast status determination device 10" in a fourth embodiment of the breast pump 100"'.

The breast pump 100"' comprises a breast unit 110"' and a base unit 120"' The breast unit 110"' and the base unit 120"' are connected via connection line 130 that includes an air-duct 140 and a power and data line in form of power cord 150.

The breast status determination device 10"' comprises a breast shield 16"', a nipple elongation measurement unit 17"' including a pressure estimation unit 18"', a battery 70, a breast status determination unit 20"' comprising a breast emptiness estimation unit 21"' arranged in the base unit 120"', and a breast status indication unit in form of an alarm light 22"'.

The breast shield 16"' has a nipple tunnel 24 in which the pressure estimation unit 18"' is arranged. FIG. 5 shows breast 12 moving away from the breast shield 16"' after the end of a milk extraction session. Breast shield connector 40 includes milk storage container 42 for storing extracted milk 44. During the milk extraction session, nipple 26 of the breast 12 is arranged in the nipple tunnel 24.

The pressure estimation unit 18"' estimates a drop of pressure within the breast shield 16"' in which the breast 12 is received during the milk extraction session. The drop of pressure depends on a volume in the nipple tunnel 24. The volume in the nipple tunnel 24 decreases as the nipple 26 elongates for a specific pressure in the breast shield 16"'. The pressure estimation unit 18"' allows to estimate the elongation of the nipple 26 based on a change of the volume in the nipple tunnel 24. The pressure estimation unit 18"' comprises two pressure sensors in this embodiment (not shown). In other embodiments the pressure estimation unit can comprise one or more pressure sensors and the pressure estimation unit can measure the specific pressure in the breast shield. This allows to measure the specific pressure in the breast shield for example if the pressure applied to the breast shield. e.g. by a pressure source such as a vacuum pump, is not known. The pressure estimation unit can furthermore measure the pressure outside of the breast shield. This allows to measure a pressure applied to the breast shield and/or a pressure of the surroundings of the breast shield.

The elongation of the nipple 26 is provided to the base unit 120"' via the power cord 150 from the pressure estimation unit 18"'.

In this embodiment battery 70 powers pressure estimation unit 18"'. Battery 70 is optional. The battery 70 is rechargeable and can be charged via the power cord 150.

The base unit 120"' comprises a breast pump control unit 50"', a vacuum pump 46, a power supply 48, and a user interface in form of touch display 52.

The breast pump control unit 50"' includes the breast emptiness estimation unit 21"'.

The breast emptiness estimation unit 21"' comprises control unit 30' with processor 34 and memory 36. The breast emptiness estimation unit 21"' uses a breast emptiness estimation function with the elongation of the nipple 26 and the specific pressure in the breast shield 16"' as input and breast emptiness as output. In other embodiments the breast estimation unit can also use other methods for estimating the breast emptiness, e.g. based on a table with values of breast emptiness in dependence of elongations of the nipple and specific pressure in the breast shield or estimating when the breast is empty by comparing the elongation of the nipple for a specific pressure in the breast shield for consecutive cycles of alternating increased pressure and reduced pressure. The breast emptiness estimation unit 21"' provides a breast emptiness status signal to the alarm light 22"'.

The alarm light 22"' provides a visual indication of the breast emptiness over time based on the breast emptiness status signal, for example providing differently colored blinking or shining lights, such as green, yellow, and red, or a continuously changing color in dependence of amount of milk left in the breast in order to indicate breast emptiness. This allows the user to decide when to end the milk extraction session.

Figure 6:
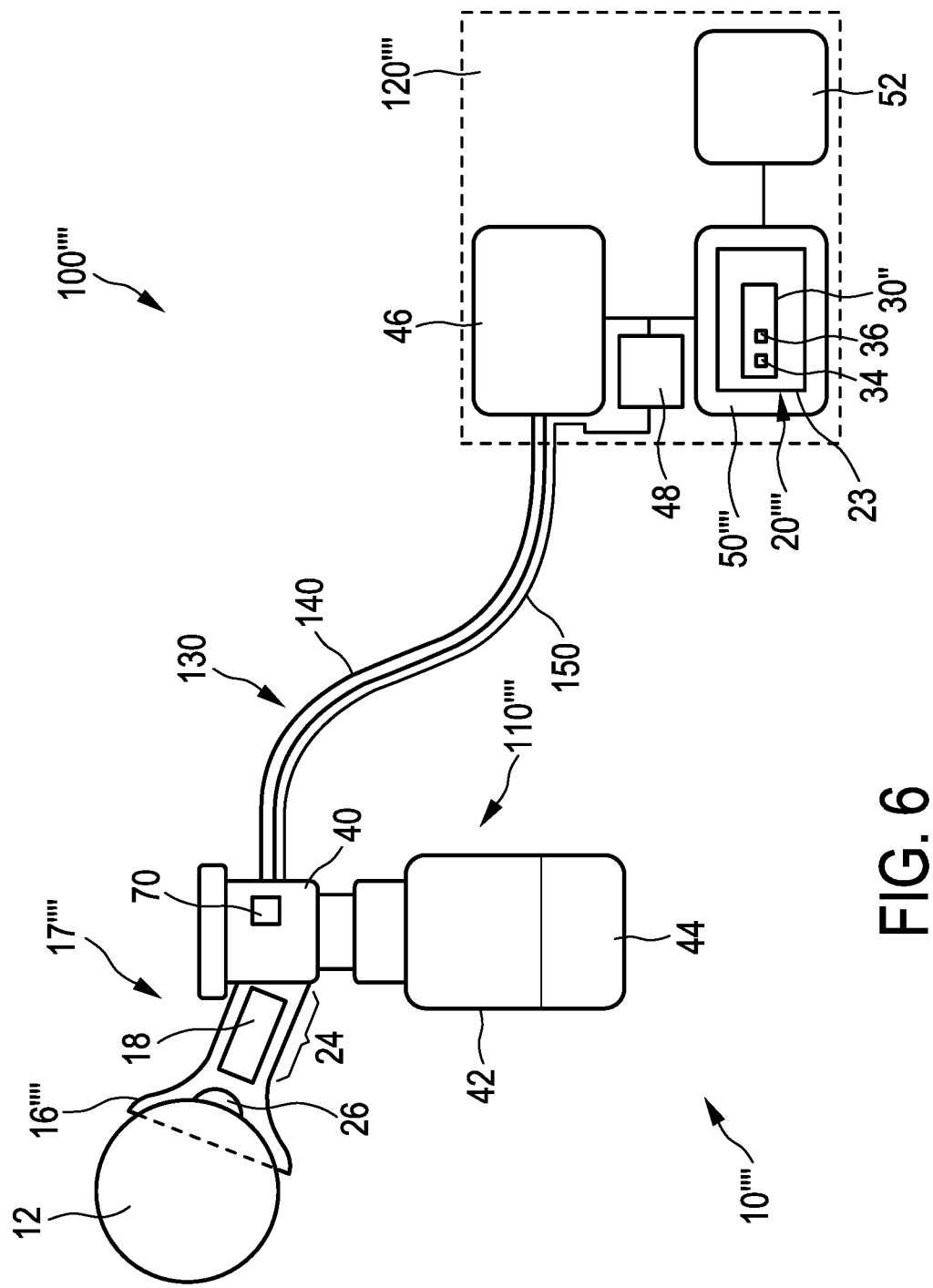
FIG. 6 shows schematically and exemplarily a fifth embodiment of the breast status determination device in a fifth embodiment of the breast pump.

FIG. 6 shows schematically and exemplarily a fifth embodiment of the breast status determination device 10"" in a fifth embodiment of the breast pump 100"".

The breast pump 100"" comprises a breast unit 110"" and a base unit 120"". The breast unit 110"" and the base unit 120"" are connected via connection line 130 that includes an air-duct 140 and a power and data line in form of power cord 150.

The breast status determination device 10"" comprises a breast shield 16"", a nipple elongation measurement unit 17"" including a camera 18, a battery 70, and a breast status determination unit 20"" comprising a MER detection unit 23 arranged in the base unit 120"".

The breast shield 16"" has a nipple tunnel 24. The camera 18 is arranged at the nipple tunnel 24 in order to record images of nipple 26 of breast 12. FIG. 6 shows the breast 12 moving away from the breast shield 16"" after the end of a milk extraction session. Breast shield connector 40 includes milk storage container 42 for storing extracted milk 44. During the milk extraction session the nipple 26 of the breast 12 is arranged in the nipple tunnel 24.

The camera 18 records images of the nipple 26 during the milk extraction session. The camera allows to estimate the elongation of the nipple 26 based on the recorded images.

The elongation of the nipple 26 measured with the nipple elongation measurement unit 17"" is provided to the base unit 120"" via the power cord 150 from the camera 18.

In this embodiment battery 70 powers the camera 18. Battery 70 is optional. The battery 70 is rechargeable and can be charged via the power cord 150.

The base unit 120"" comprises a breast pump control unit 50"", a vacuum pump 46, a power supply 48, and a user interface in form of touch display 52.

The breast pump control unit 50"" includes the MER detection unit 23.

The MER detection unit 23 comprises control unit 30" with processor 34 and memory 36. The MER detection unit 23 detects whether a MER is present or absent based on the elongation of the nipple 26, i.e. the MER detection unit 23 detects absence or presence of the MER. The MER detection unit 23 compares the elongation of the nipple 26 for a specific pressure in the breast shield 16"" between subsequent cycles of alternating increased pressure and reduced pressure and determines whether the breast is not empty. If the breast is not empty and the elongation of the nipple 26 for a specific pressure in the breast shield 16"" does not change between the subsequent cycles of alternating increased and reduced pressure, absence of the MER is detected. If the elongation of the nipple 26 for a specific pressure in the breast shield 16"" changes between the subsequent cycles of alternating increased and reduced pressure, presence of MER is detected. In this embodiment the breast is defined to be not empty if the duration of the current milk extraction session is below a predetermined duration threshold value of 3 minutes. In other embodiments the predetermined duration threshold value can for example be 2 minutes or 1 minute. In other embodiments the breast status determination unit can comprise a breast emptiness estimation unit for estimating a breast emptiness of the breast of the user. The breast emptiness estimation unit can be used for determining whether the breast is not empty. In other embodiments the breast status determination unit can determine a status of the breast of the user. The determined status of the breast of the user can be the estimated breast emptiness of the breast of the user, the detected presence or absence of the MER, or the estimated breast emptiness of the breast of the user and the detected presence or absence of the MER of the breast of the user.

The MER detection unit 23 adapts a breast shield setting in dependence of the presence or absence of the MER. In other embodiments the breast status determination unit can be configured for adapting the breast shield setting in dependence of the determined status of the breast of the user, e.g. based on breast emptiness and/or absence or presence of the MER. In this embodiment the MER detection unit 23 is configured to adapt the breast shield setting in order to stimulate the MER when absence of the MER is detected and to improve the extraction of milk, when presence of the MER is detected. The breast shield setting for stimulating the MER is in this embodiment a high reduced pressure at a high frequency of alternating cycles of increased pressure and reduced pressure, such that a low suction force is applied to the nipple with a high frequency. In other embodiments additionally or alternatively a massaging motion of a collapsible membrane can be used for stimulating the MER. The breast shield setting for extracting milk is in this embodiment a very low reduced pressure at a low frequency of alternating cycles of increased pressure and reduced pressure, such that a high suction force is applied to the nipple with a low frequency. In other embodiments additionally or alternatively a peristaltic motion of a collapsible membrane can be used for extracting milk from the breast. This allows to improve the triggering of the MER and the extraction of the milk during the milk extraction session.

Figure 7:
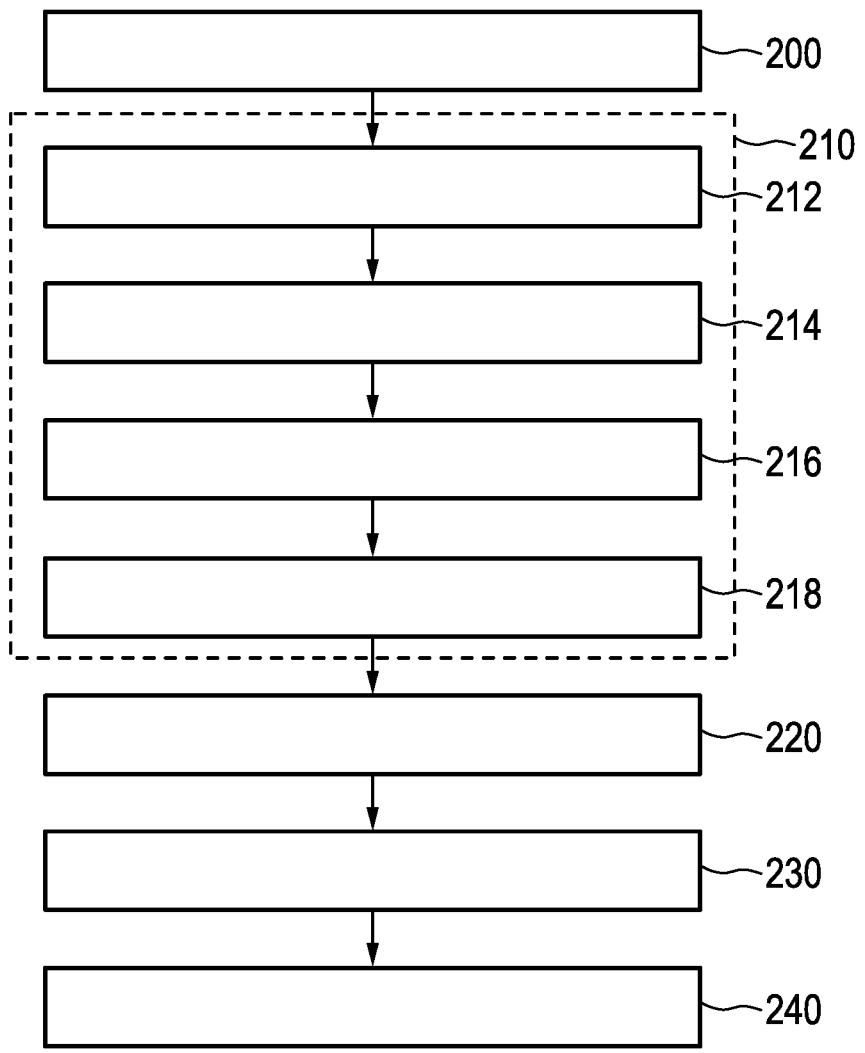
FIG. 7 shows an embodiment of the method for operating the breast pump.

FIG. 7 shows an embodiment of the method for operating a breast pump. The breast pump comprises a breast status determination device and a pressure source. The breast status determination device comprises a breast shield for receiving a breast of a user therein, a nipple elongation measurement unit for measuring an elongation of a nipple of the breast received in the breast shield for a specific pressure in the breast shield during a milk extraction session, and a breast status determination unit in form of a breast emptiness estimation unit. The nipple elongation measurement unit has a camera, a distance sensor in form of an ultrasound sensor, a pressure estimation unit, and a nipple shape measurement unit. In other embodiments the ultrasound sensor can be replaced by another distance sensor, e.g., a proximity sensor, such as a radar, a sonar, or the like. In other embodiments the nipple elongation measurement unit can have only one of the camera, the distance sensor, the pressure estimation unit, and the nipple shape measurement unit. In this embodiment the nipple shape measurement unit has a collapsible membrane and a membrane shape measurement unit with strain sensors. In other embodiments the membrane shape measurement unit can be an accelerometer.

In step 200 of the method, cycles of alternating increased pressure and reduced pressure are generated in the breast shield to extract milk from the breast of the user. The pressure source is used for generating cycles of alternating increased pressure and reduced pressure in the breast shield in order to mimic a suckling pattern of sucking and release that stimulates the MER and to extract milk from the nipple of the breast. In this embodiment the pressure source is an electronic vacuum pump. In other embodiments the vacuum pump can be a manually operated vacuum pump, such as a vacuum pump operated with a handle.

In step 210 the elongation of the nipple of the user for a specific pressure in the breast shield is measured during the milk extraction session. Four different ways for measuring the elongation of the nipple in this embodiment are performed in the sub steps 212, 214, 216, and 218.

In step 212 images of the nipple of the breast of the user are recorded during the milk extraction session. The elongation of the nipple of the breast of the user for the specific pressure in the breast shield during the milk extraction session is measured based on the recorded images.

In step 214 time of flight of ultrasound between a tip of the nipple of the breast of the user and a fixed point arranged opposite of the tip and axially aligned to the direction in which the nipple elongates during the milk extraction session is measured. The elongation of the nipple of the breast of the user for the specific pressure in the breast shield during the milk extraction session is measured based on the measured time of flight of the ultrasound. In other embodiments the distance between the fixed point and the tip of the nipple of the breast of the user during the milk extraction session can be measured based on changes of an electromagnetic field or based on time of flight measurements of other signals, such as an infrared signal, during the milk extraction session.

In step 216 a pressure drop within the breast shield in which the breast of the user is received is estimated during the milk extraction session. The elongation of the nipple of the breast of the user for the specific pressure in the breast shield during the milk extraction session is measured based on the estimated pressure drop within the breast shield.

In step 218 a shape of the nipple is measured during the milk extraction session. The elongation of the nipple of the breast of the user for the specific pressure in the breast shield during the milk extraction session is measured based on the measured shape of the nipple for the specific pressure in the breast shield during the milk extraction session. The shape of the nipple is measured by measuring a shape of a collapsible membrane conforming to the shape of the breast during the milk extraction session. The shape of the collapsible membrane is in this embodiment measured by measuring strain at various positions on the collapsible membrane and deriving a local curvature of the part of the collapsible membrane in physical contact with the nipple during the milk extraction session in order to measure the elongation of the nipple for the specific pressure in the breast shield during the milk extraction session. Based on the local curvature the shape of the collapsible membrane is measured during the milk extraction session. From the shape of the collapsible membrane, the shape of the nipple is derived, which is used to measure the elongation of the nipple for the specific pressure in the breast shield during the milk extraction session. In other embodiments the shape of the nipple during the milk extraction session can be measured using an accelerometer for estimating the shape of the collapsible membrane.

Only one of the sub steps 212, 214, 216, and 218 has to be performed in order to measure the elongation of the nipple for the specific pressure in the breast shield. Performing more than one of the steps 212, 214, 216, and 218 allows to increase the accuracy of the measurement of the elongation of the nipple for the specific pressure in the breast shield as an average value, e.g. a weighted average value, for the elongation of the nipple can be determined based on the four different measured elongations of the nipple for the specific pressure in the breast shield.

In step 220 the shape of the breast is measured during the milk extraction session in order to improve estimation of breast emptiness. Measuring the shape of the breast in this embodiment is performed by measuring a shape of the collapsible membrane enclosing the breast and conforming to the shape of the breast during the milk extraction session. The shape is in this embodiment measured by measuring strain at various positions on the collapsible membrane and deriving a local curvature of the collapsible membrane at the positions. Based on the local curvature the shape of the collapsible membrane is measured during the milk extraction session. The shape of the collapsible membrane is used to provide additional information for estimating the breast emptiness of the breast of the user. In other embodiments an accelerometer and the data obtained from it can be used to measure the shape of the breast and to provide additional information for estimating the breast emptiness of the breast of the user. Step 220 is optional. Steps 210 and 220 can be performed in interchanged order.

In step 230 breast emptiness of the breast of the user is estimated based on the elongation of the nipple of the breast of the user. Additionally in this embodiment the shape of the breast is considered for estimating the breast emptiness. In this embodiment a breast emptiness estimation function is provided for estimating the breast emptiness. The breast emptiness estimation function is trained using machine learning with training data recorded in previous milk extraction sessions. Alternatively other methods can be used in order to generate a breast emptiness estimation function that allows to estimate the breast emptiness based on the elongation of the nipple and the specific pressure in the breast shield. Yet in other embodiments a table with values of breast emptiness in dependence of elongations of the nipple and specific pressure in the breast shield can be used to estimate the breast emptiness based on the measured elongation of the nipple for the specific pressure in the breast shield. The table can be based on recorded data from previous milk extraction session. In yet other embodiments in step 230 it can be estimated when the breast is empty by estimating when the elongation of the nipple for the specific pressure in the breast shield does not change anymore for a predetermined number of cycles or a predetermined amount of time. e.g., when the change in the elongation of the nipple for the specific pressure in the breast shield is below a predetermined threshold value for a predetermined number of consecutive cycles of alternating increased pressure and reduced pressure. In yet other embodiments step 230 can be replaced by a step of determining a status of the breast of the user based on the elongation of the nipple of the breast of the user. The determined status of the breast of the user can be the estimated breast emptiness of the breast of the user, a detected presence or absence of a MER, or the estimated breast emptiness of the breast of the user and the detected presence or absence of the MER of the breast of the user.

In step 240 it is indicated when the breast of the user is empty. In this embodiment a switch-off signal is generated that switches off the breast pump. In other embodiments the breast emptiness of the breast of the user can be indicated and the indication can for example be provided as a visual and/or an audio signal, such as an alarm light or an alarm sound. This allows to end the milk extraction session when the breast is empty or when the breast emptiness reached a level at which the user decides to end the milk extraction session. Step 240 is optional. In other embodiments the determined status of the breast of the user is indicated.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like generating cycles of alternating increased pressure and reduced pressure in the breast shield to extract milk from the breast of the user, measuring elongation of the nipple of the user for the specific pressure in the breast shield during the milk extraction session, determining a status of the breast of the user based on the elongation of the nipple of the breast of the user, estimating breast emptiness of the breast of the user based on the elongation of the nipple of the breast of the user, indicating the determined status of the breast of the user, indicating the breast emptiness of the breast of the user, recording images of the nipple of the breast of the user during the milk extraction session, measuring the distance between a tip of the nipple of the breast of the user and a fixed point arranged opposite of the tip and axially aligned to the direction in which the nipple elongates during the milk extraction session, measuring time of flight of ultrasound between a tip of the nipple of the breast of the user and a fixed point arranged opposite of the tip and axially aligned to the direction in which the nipple elongates during the milk extraction session, estimating a pressure drop within the breast shield in which the breast of the user is received during the milk extraction session, measuring the shape of the breast during the milk extraction session in order to improve estimation of breast emptiness, et cetera performed by one or several units or devices can be performed by any other number of units or devices. These operations and/or the method can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet. Ethernet. or other wired or wireless telecommunication systems.

Any reference signs in the claims should not be construed as limiting the scope.

The present invention relates to a breast status determination device. The breast status determination device comprises a breast shield, a nipple elongation measurement unit, and a breast status determination unit. The breast shield can receive a breast of a user therein. The nipple elongation measurement unit can measure an elongation of a nipple of the breast received in the breast shield for a specific pressure in the breast shield during a milk extraction session. The breast status determination unit can determine a status of the breast based on the elongation of the nipple. The breast status determination device can allow estimating the amount of milk left in the breast during the milk extraction session, when the breast is empty, and whether a milk ejection reflex is present or absent in the breast.

The invention claimed is:

1. A breast status determination device comprising:
a breast shield for receiving a breast of a user therein,
a nipple elongation measurement unit configured for measuring an elongation of a nipple of the breast received in the breast shield for a specific pressure in the breast shield during a milk extraction session, and
a breast status determination unit configured for determining an estimated breast emptiness of the breast of the user, a presence an absence of a milk ejection reflex, or the estimated breast emptiness of the breast of the user and the presence or the absence of the milk ejection reflex of the breast of the user as a status of the breast of the user based on the elongation of the nipple of the breast of the user.

2. The breast status determination device according to claim 1, wherein the breast status determination unit is configured for adapting a breast shield setting dependent on the status of the breast of the user.

3. The breast status determination device according to claim 2, comprising a breast status indication unit configured for indicating to the user the status of the breast of the user.

4. The breast status determination device according to claim 3, wherein the nipple elongation measurement unit is configured for measuring the elongation of the nipple of the breast received in the breast shield for the specific pressure in the breast shield during the milk extraction session based on an indirect measurement.

5. The breast status determination device according to claim 3, wherein the nipple elongation measurement unit comprises:
a camera for recording images of the nipple of the breast of the user during the milk extraction session,
a distance sensor arranged opposite of a tip of the nipple of the breast of the user and axially aligned to a direction in which the nipple elongates during the milk extraction session and wherein the distance sensor is configured for measuring a distance between the distance sensor and the tip of the nipple of the breast of the user during the milk extraction session,
a pressure estimation unit for estimating a drop of pressure within the breast shield in which the breast of the user is received during the milk extraction session, and/or
a nipple shape measurement unit for measuring a shape of the nipple of the breast of the user during the milk extraction session.

6. The breast status determination device according to claim 5, wherein the breast status determination unit comprises a memory storing at least one value of breast emptiness dependent on the elongation of the nipple and the specific pressure in the breast shield or a breast emptiness estimation function with the elongation of the nipple and the specific pressure in the breast shield as input and the breast emptiness as output.

7. A breast pump for extracting milk comprising:
the breast status determination device according to claim 1, and
a pressure source in air-ducting connection to the breast shield for generating cycles of alternating increased pressure and reduced pressure in the breast shield to extract the milk from the breast of the user.

8. The breast pump according to claim 7, further comprising a breast pump control unit configured to synchronize a moment of sampling of the elongation of the nipple with the specific pressure in the breast shield generated by the pressure source or to provide sampling of the elongation of the nipple with a sampling rate which is at least 3 times higher than a frequency of the cycles of the alternating increased pressure and reduced pressure in the breast shield generated by the pressure source.

9. A method for operating the breast pump according to claim 7, the method comprising:
generating the cycles of the alternating increased pressure and reduced pressure in the breast shield to extract milk from the breast of the user,
measuring the elongation of the nipple of the breast received in the breast shield for the specific pressure in the breast shield during the milk extraction session, and
determining the estimated breast emptiness of the breast of the user, the presence or the absence of the milk ejection reflex, or the estimated breast emptiness of the breast of the user and the presence or the absence of the milk ejection reflex of the breast of the user as the status of the breast of the user based on the elongation of the nipple of the breast of the user.

10. The method according to claim 9, further comprising indicating the status of the breast of the user.

11. The method according to claim 10, further comprising:
recording images of the nipple of the breast of the user during the milk extraction session, wherein the elongation of the nipple of the breast of the user for the specific pressure in the breast shield during the milk extraction session is measured based on the recorded images,
measuring a distance between a tip of the nipple of the breast of the user and a fixed point arranged opposite of the tip and axially aligned to a direction in which the nipple elongates during the milk extraction session, wherein the elongation of the nipple of the breast of the user for the specific pressure in the breast shield during the milk extraction session is measured based on the measured distance between the tip of the nipple and the fixed point,
estimating a pressure drop within the breast shield in which the breast of the user is received during the milk extraction session, wherein the elongation of the nipple of the breast of the user for the specific pressure in the breast shield during the milk extraction session is measured based on the estimated pressure drop within the breast shield, and/or
measuring a shape of the nipple during the milk extraction session, wherein the elongation of the nipple of the breast of the user for the specific pressure in the breast shield during the milk extraction session is measured based on the measured shape of the nipple.

12. A breast pump comprising:
a breast shield for receiving a breast of a user therein;
a pressure source in air-ducting connection to the breast shield;
a processor; and
a tangible, non-transitory computer readable medium that stores instructions, which when executed by the processor, causes the processor to:
generate cycles of alternating increased pressure and reduced pressure in the breast shield to extract milk from the breast of the user;

measure an elongation of a nipple of the breast received in the breast shield for a specific pressure in the breast shield during a milk extraction session, and determine an estimated breast emptiness of the breast of the user, a presence or an absence of a milk ejection reflex, or the estimated breast emptiness of the breast of the user and the presence or the absence of the milk ejection reflex of the breast of the user as a status of the breast of the user based on the elongation of the nipple of the breast of the user.

13. The breast pump of claim 12, wherein the instructions further cause the processor to indicate the status of the breast of the user.

14. The breast pump of claim 12, wherein the instructions further cause the processor to:

record images of the nipple of the breast of the user during the milk extraction session, wherein the elongation of the nipple of the breast of the user for the specific pressure in the breast shield during the milk extraction session is measured based on the recorded images;

measure a distance between a tip of the nipple of the breast of the user and a fixed point arranged opposite of the tip and axially aligned to a direction in which the nipple elongates during the milk extraction session, wherein the elongation of the nipple of the breast of the user for the specific pressure in the breast shield during the milk extraction session is measured based on the measured distance between the tip of the nipple and the fixed point;

estimate a pressure drop within the breast shield in which the breast of the user is received during the milk extraction session, wherein the elongation of the nipple of the breast of the user for the specific pressure in the breast shield during the milk extraction session is measured based on the estimated pressure drop within the breast shield, and/or measure a shape of the nipple during the milk extraction session, wherein the elongation of the nipple of the breast of the user for the specific pressure in the breast shield during the milk extraction session is measured based on the measured shape of the nipple.

* * * * *